(12) United States Patent  (10) Patent No.: US 7,936,456 B2
Narisada  (45) Date of Patent: May 3, 2011

(54) PARTICLE ANALYZER AND PARTICLE ANALYZING METHOD

(75) Inventor: Noriyuki Narisada, Akashi (JP)

(73) Assignee: Sysmex Corporation, Tokyo (JP)

( * ) Notice: Subject to any disclaimer, the term of this patent is extended or adjusted under 35 U.S.C. 154(b) by 439 days.

(21) Appl. No.: 12/022,658

(22) Filed: Jan. 30, 2008

(65) Prior Publication Data

US 2008/0180653 A1 Jul. 31, 2008

(30) Foreign Application Priority Data

Jan. 31, 2007 (JP) ................................. 2007-022439

(51) Int. Cl.
G01N 1/00 (2006.01)
G01N 21/66 (2006.01)
(52) U.S. Cl. ........................... 356/338; 356/336; 422/73
(58) Field of Classification Search .............. 356/36–41, 356/335–340, 246, 432–437; 422/73, 102; 436/10, 8, 63, 164, 172; 382/133, 134, 286
See application file for complete search history.

(56) References Cited

U.S. PATENT DOCUMENTS

| | | | | |
|---|---|---|---|---|
| 5,488,469 A | * | 1/1996 | Yamamoto et al. | 356/72 |
| 5,690,105 A | * | 11/1997 | Shibata et al. | 600/300 |
| 5,731,867 A | * | 3/1998 | Katayama | 356/73 |
| 5,878,160 A | * | 3/1999 | Horiuchi et al. | 382/133 |
| 5,888,823 A | * | 3/1999 | Matsumoto et al. | 436/10 |
| 6,159,740 A | * | 12/2000 | Hudson et al. | 436/63 |
| 6,365,106 B1 | * | 4/2002 | Nagai | 422/73 |
| 6,573,102 B2 | * | 6/2003 | Li et al. | 436/17 |
| 6,979,570 B2 | | 12/2005 | Narisada | |
| 7,405,082 B2 | * | 7/2008 | Mizukami et al. | 436/63 |
| 7,601,539 B2 | * | 10/2009 | Kawate | 436/8 |
| 7,618,587 B2 | * | 11/2009 | Kawate | 422/73 |
| 2003/0143117 A1 | * | 7/2003 | Nagai et al. | 422/73 |

FOREIGN PATENT DOCUMENTS

JP 2003-106984 A 4/2004

* cited by examiner

Primary Examiner — Sang Nguyen
(74) Attorney, Agent, or Firm — Sughrue Mion, PLLC

(57) ABSTRACT

The present invention is to present a particle analyzer that is capable of classifying and counting particles contained in a sample more accurately. The blood analyzer 1 includes: measuring unit 2 for obtaining a plurality of characteristic information of each of particles contained in a sample by measuring a measurement sample prepared from the sample; data processing unit 3 for obtaining a particle number of a specific kind of particles and each particle number of a plural kinds of particles different from the specific kind of particles, and determining a target kind of particles, whose particle number is corrected, from the plural kinds of particles, based on information obtained by the measuring unit 2, and correcting a particle number of the target kind of particles by using the particle number of the specific kind of particles.

20 Claims, 16 Drawing Sheets

PARTICLE ANALYZER AND PARTICLE ANALYZING METHOD

FIELD OF THE INVENTION

The present invention relates to a particle analyzer and a particle analyzing method, in particular to a particle analyzer and a particle analyzing method for classifying and counting particles contained in a sample based on characteristic parameters of the particles.

BACKGROUND

Conventionally, classification and counting of particles contained in the sample such as blood and urine is performed. For instance, Japanese Laid-Open Patent Publication No. 2003-106984 discloses a particle analyzer for irradiating light on a liquid containing particles flowing while being surrounded by sheath solution, obtaining characteristic parameters from each particle, and generating a scattergram using the characteristic parameters. The particle analyzer classifies and counts the particles by classifying the particles appearing on the generated scattergram into a plurality of particle groups, and counting the particles of each particle group.

The particle analyzer disclosed in Japanese Laid-Open Patent Publication No. 2003-106984 determines classification abnormality of the particles appearing on the scattergram and displays the determination result on a display to prevent erroneous analysis, when measuring a blood sample containing nucleated red blood cells.

Japanese Laid-Open Patent Publication No. 2003-106984 describes that, in the blood sample containing the nucleated red blood cells, the nucleated red blood cells appear in a distribution region of the lymphocytes and in a region on the lower part thereof and does not appear in a distribution region of the neutrophilic leucocytes on the scattergram for classifying white blood cells into four classifications.

However, in the blood sample of a patient with a special disease, the nucleated red blood cells sometimes appear in a distribution region of the neutrophilic leukocytes or in a distribution region of the red blood cell ghosts (red blood cell particles after hemolysis) on the scattergram. Thus, in the particle analyzer disclosed in Japanese Laid-Open Patent Publication No. 2003-106984, the classification abnormality of the particles is not capable of be accurately determined when measuring the special blood sample in which the nucleated red blood cells appear in the distribution region of the neutrophilic leucocytes or in the distribution region of the red blood cell ghosts.

SUMMARY

A first aspect of the present invention is a particle analyzer, comprising: characteristic information obtaining means for obtaining a plurality of characteristic information of each of particles contained in a sample by measuring a measurement sample prepared from the sample; particle number obtaining means for obtaining a particle number of a specific kind of particles contained in the sample and each particle number of a plural kinds of particles contained in the sample, the plural kinds of particles being different from the specific kind of particles, based on information obtained by the characteristic information obtaining means; target particle determining means for determining a target kind of particles, whose particle number is corrected, from the plural kinds of particles, based on information obtained by the characteristic information obtaining means; and correcting means for correcting a particle number of the target kind of particles obtained by the particle number obtaining means, by using the particle number of the specific kind of particles.

A second aspect of the present invention is a particle analyzer, comprising: characteristic information obtaining means for obtaining a plurality of characteristic information of each of particles contained in a sample by measuring a measurement sample prepared from the sample; particle number obtaining means for obtaining a particle number of a specific kind of particles contained in the sample and each particle number of a plural kinds of particles contained in the sample, the plural kinds of particles being different from the specific kind of particles, based on information obtained by the characteristic information obtaining means; correction degree determining means for determining a correction degree for correcting the each particle number of the plural kinds of particles based on information obtained by the characteristic information obtaining means; and correcting means for correcting the each particle number of the plural kinds of particles, based on the particle number of the specific kind of particles and the correction degree.

A third aspect of the present invention is a particle analyzing method, comprising steps of: (a) obtaining a plurality of characteristic information of each of particles contained in a sample by measuring a measurement sample prepared from the sample; (b) obtaining a particle number of a specific kind of particles contained in the sample and each particle number of a plural kinds of particles contained in the sample, the plural kinds of particles being different from the specific kind of particles, based on information obtained in step (a); (c) determining a target kind of particles, whose particle number is corrected, from the plural kinds of particles, based on information obtained in step (a); and (d) correcting a particle number of the target kind of particles obtained in step (b) by using the particle number of the specific kind of particles.

DETAILED DESCRIPTION OF THE EMBODIMENT

The preferred embodiments of the present invention will now be described based on the drawings.

Figure 1:
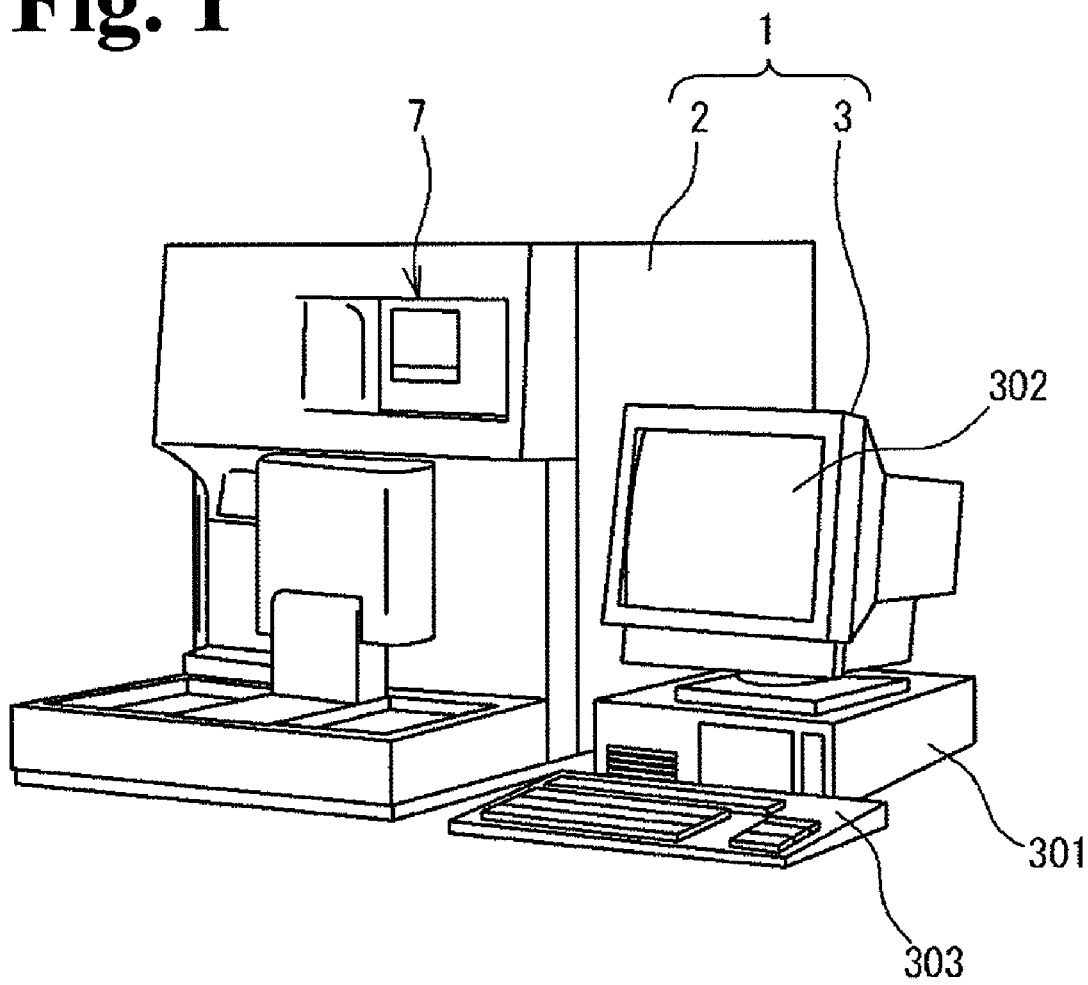
FIG. 1 is a perspective view showing a blood analyzer.

FIG. 1 shows a blood analyzer 1. The blood analyzer 1 is configured as a multiple automatic blood cell analyzer for performing blood test, where measurement of the blood sample accommodated in a sample container (blood collection tube) is performed, and analysis of the relevant measurement result is performed.

The analyzer 1 includes a measuring unit 2 having a function of measuring the blood or the sample, and a data processing unit 3 for processing the measurement result output from the measuring unit 2 and obtaining an analysis result.

In FIG. 1, the measuring unit 2 and the data processing unit 3 are configured as separate devices, but may be configured as an integrated device.

Figure 2:
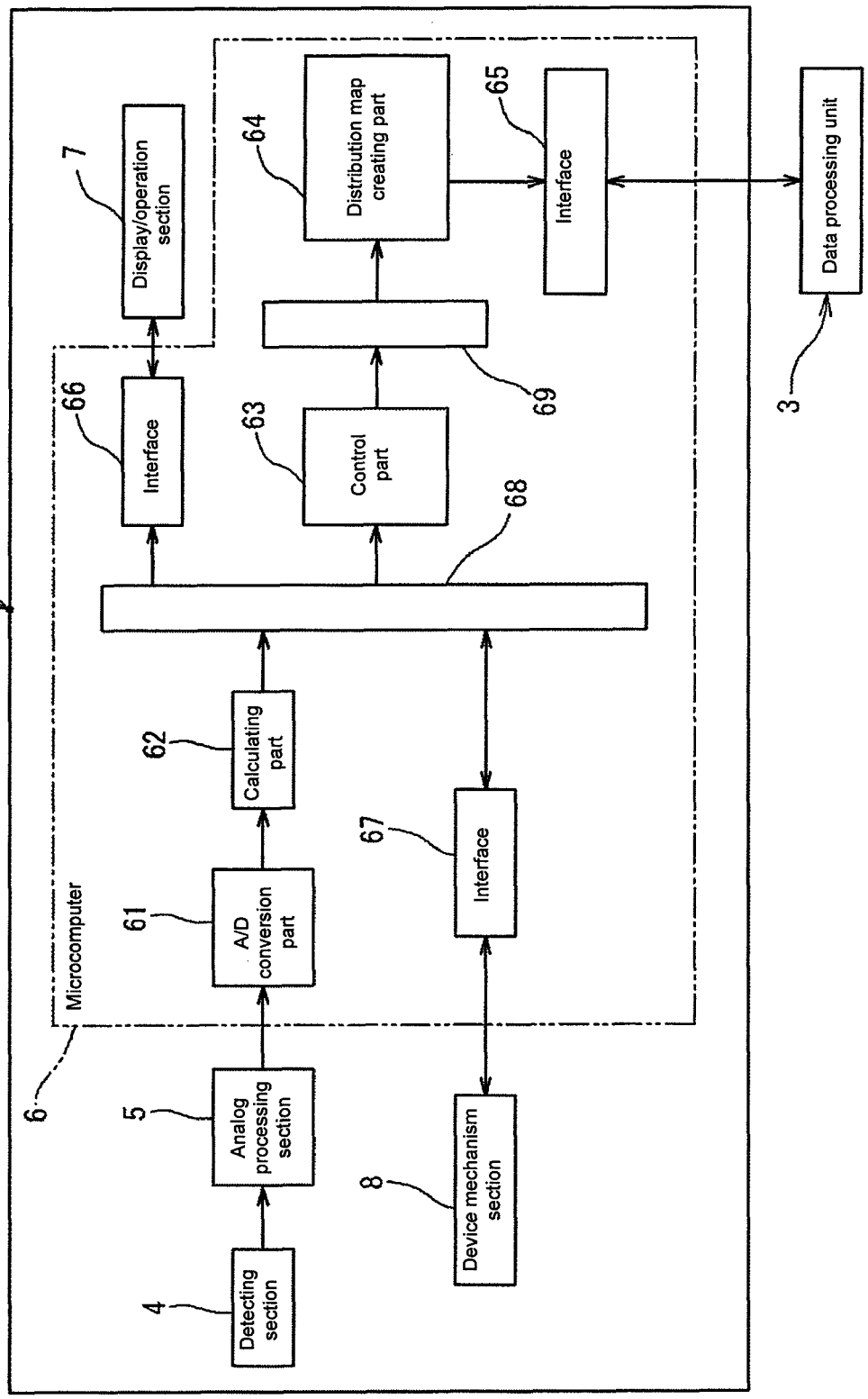
FIG. 2 is a functional block diagram of a measuring unit.

FIG. 2 shows a block diagram of a measuring unit 2 of the analyzer 1. As shown in FIG. 2, the measuring unit 2 includes a blood cell detecting section 4, an analog processing section 5 for processing a detection signal output from the detecting section 4, a microcomputer 6, a display/operation section 7, and a device mechanism section 8 for blood measurement.

The detecting section 4 includes a white blood cell detecting part for detecting white blood cells. The white blood cell detecting part is also used to detect nucleated red blood cells. In addition to the white blood cell detecting part, the detecting section 4 also includes a RBC/PLT detecting part for measuring number of red blood cells and number of platelets, an HGB detecting part for detecting hemoglobin content in the blood, and an IMI detecting part for detecting immature leukocytes.

The white blood cell detecting part is configured as an optical detecting part, and specifically, is configured as a detecting part adopting flow cytometry method.

Cytometry relates to measuring physical property and chemical property of cells and other biological particles, and flow cytometry is a method of performing measurement by passing such particles into a narrow flow.

Figure 3:
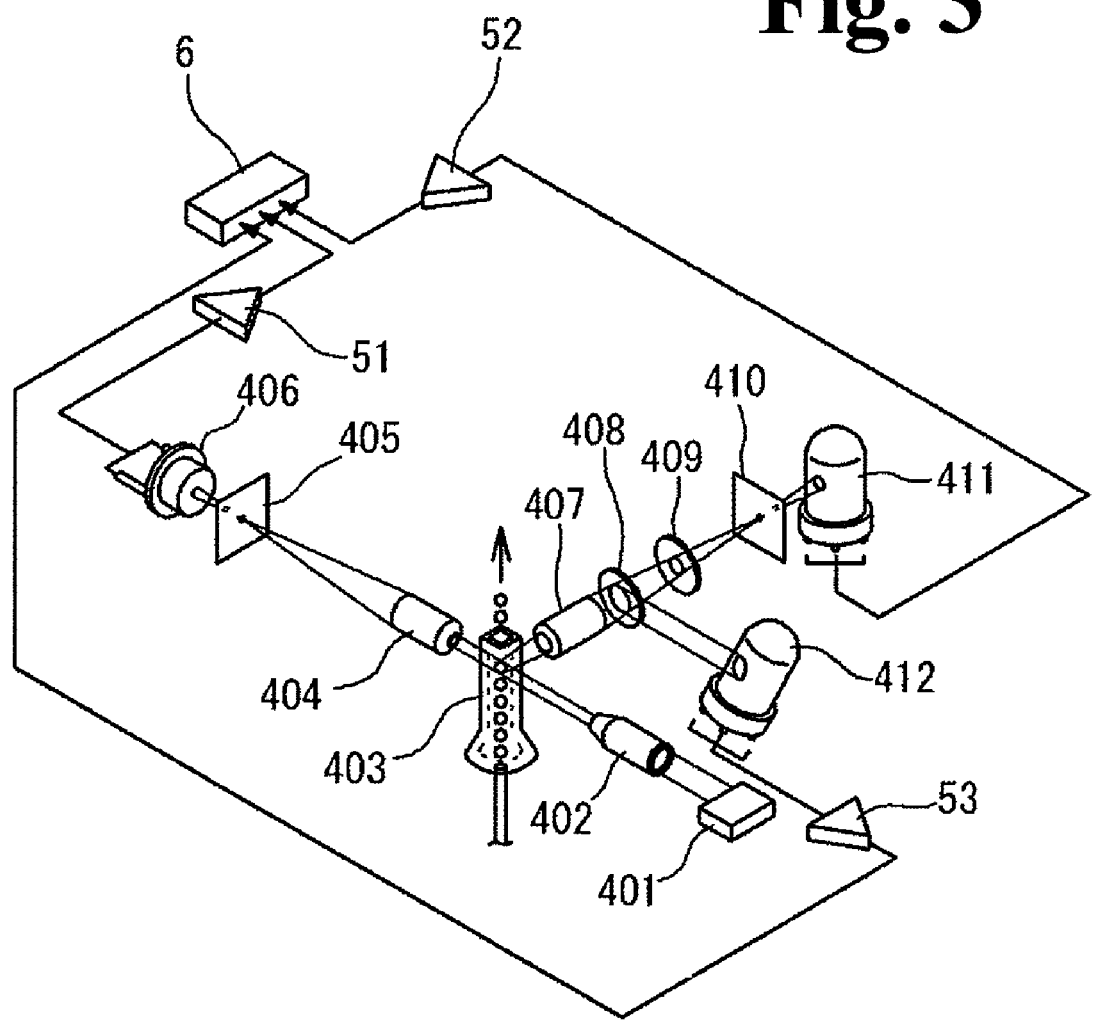
FIG. 3 is a configuration view of a detecting section.

FIG. 3 shows an optical system of the white blood cell detecting part. In the figure, a beam exit from a laser diode 401 is irradiated on the blood cells passing through a sheath flow cell 403 via a collimator lens 402.

In the white blood cell detecting part, the forward scattered light, lateral scattered light, and lateral fluorescence emitted from the blood cells in the sheath flow cell irradiated with the light are detected. The forward scattered light intensity, the lateral scattered light intensity, and the lateral fluorescence intensity obtained from the detected forward scattered light, the lateral scattered light, and the lateral fluorescence are used as characteristic parameters of the blood cells.

Light scattering is a phenomenon that occurs when particles such as blood cells exist as an obstacle in the advancing direction of the light and the light changes the advancing direction. The characteristic information related to size of the particle and component contained in the particle are obtained by detecting the scattered light. The forward scattered light is the scattered light emitted from the particle in a direction substantially the same as the advancing direction of the irradiated light. The characteristic information related to the size of the particle (blood cell) is obtained from the forward scattered light. The lateral scattered light is the scattered light emitted from the particle in a direction substantially perpendicular to the advancing direction of the irradiated light. When the laser light is irradiated on the blood cell particle, the lateral scattered light intensity reflects the complexity of the inside of the cell (shape, size, density of core and amount of granules). Thus, characteristic information related to the inside of the particle can be obtained from the lateral scattered light. Therefore, the blood cells can be classified and the number of blood cells can be measured by using the forward scattered light intensity and the lateral scattered light intensity. In the present embodiment, the forward scattered light and the lateral scattered light are used as the scattered light, but the present invention is not limited thereto, and scattered light of any angle with respect to the optical axis of the light transmitting through the sheath flow cell from the light source may be used as long as the scattered light signal representing features of the particle necessary for analysis is obtained.

When the light is irradiated on fluorescent substances such as stained blood cells, fluorescence having a wavelength longer than the wavelength of the irradiated light is emitted. The fluorescence intensity is stronger if satisfactorily stained. The characteristic information related to the degree of stain of the blood cells can be obtained by measuring such fluorescence intensity emitted from the blood cell. Therefore, classification of white blood cells and other analysis can be performed by using the (lateral) fluorescence intensity.

As shown in FIG. 3, the forward scattered light emitted from the blood cell (white blood cell or nucleated red blood cell) passing through the sheath flow cell 403 is received by a photodiode (forward scattered light receiving part) 406 via a light collecting lens 404 and a pin hole 405.

The lateral scattered light is received by a photo-multiplier (lateral scattered light receiving part) 411 via a light collecting lens 407, a dichroic mirror 408, an optical filter 409, and a pin hole 410.

The lateral fluorescence is received by a photo-multiplier (lateral fluorescence receiving part) 412 via the light collecting lens 407 and the dichroic mirror 408.

The received light signals output from each light receiving part 406, 411, and 412 are respectively subjected to analog processing such as amplification/waveform processing by the analog processing section 5 including amplifiers 51, 52, 53, and the like, and provided to the microcomputer 6.

The microcomputer 6 includes an A/D conversion part 61 for converting the received light signal provided from the analog processing section 5 to a digital signal. The output of the A/D conversion part 61 is provided to a calculating part 62 of the microcomputer 6, and a calculation of performing a predetermined process on the received light signal is performed in the calculating part 62.

The microcomputer 6 includes a control part 63 including a control processor and a memory for the control processor operation, and a distribution map creating part 64 including a distribution map creating processor and a memory for the distribution map creating processor operation.

The control part 63 controls the device mechanism section 8 including a sampler (not shown) for automatically supplying the blood collection tube, fluid system for preparing/measuring the sample, and the like, and also performs other controls.

The distribution map creating part 64 creates a two-dimensional scattergram (non-classified) based on the detection signal output from the detecting section 4. The distribution map creating part 64 is connected to the data processing unit 3 by way of an external interface 65, and transmits the measurement result such as the created scattergram to the data processing unit 3.

Furthermore, the microcomputer 6 has an interface 66 interposed between itself and the display/operation section 7, and an interface 67 interposed between itself and the device mechanism section 8.

The calculating part 62, the control part 63, and the interfaces 66, 67 are connected by way of a bus 68, and the control part 63 and the distribution map creating part 64 are connected by way of a bus 69.

The measuring unit 2 of the analyzer 1 of the present embodiment performs a first measurement (NRBC measurement) as a measurement of the nucleated red blood cells (NRBC), and a second measurement (DIFF measurement) as a measurement of the blood white cells, and a third measurement (WBC/BASO measurement) as the measurement of white blood cells with respect to the same blood sample. The first to the third measurements start when the user pushes a start button (not shown) arranged in the device mechanism section 8. The white blood cells are broadly classified into lymphocytes, monocytes, and granulocytes. Furthermore, the granulocytes are classified into neutrophilic leucocytes, basophilic leucocytes, and eosinophilic leukocytes according to the stainability of the granules.

The first measurement (NRBC measurement) will be described first.

Figure 4:
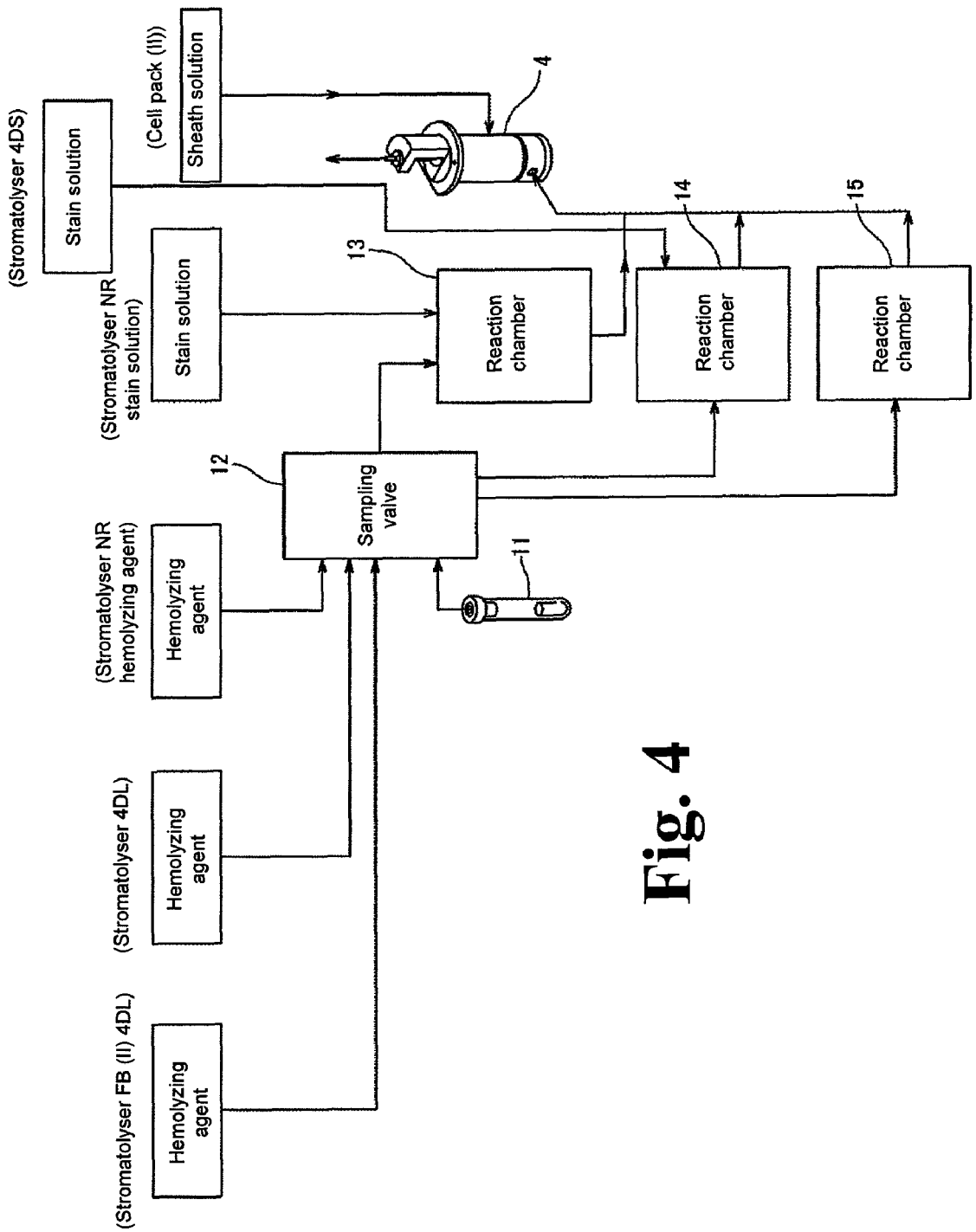
FIG. 4 is a view showing a flow of NRBC measurement, DIFF measurement, and WBC/BASO measurement.

FIG. 4 shows a flow of the NRBC measurement, the DIFF measurement, and the WBC/BASO measurement by the analyzer 1. In the NRBC measurement, a first measurement sample in which a first reagent for the first measurement (NRBC measurement) is mixed with the blood sample is prepared, and the first measurement sample is measured by the white blood cell detecting part.

In FIG. 4, the blood sample in a blood collection tube 11 is taken into a sampling valve 12 through an intake pipette (not shown). The blood sample taken in is distributed into three aliquots with the sampling valve 12. In the sampling valve 12, a first aliquot is diluted with a predetermined amount of hemolyzing agent (Stromatolyser NR hemolyzing agent manufactured by Sysmex Co.) serving as the first reagent, and conveyed to a reaction chamber 13 as diluted sample. A predetermined amount of stain solution (Stromatolyser NR staining solution manufactured by Sysmex Co.) serving as another first reagent is supplied to the reaction chamber 13, and the diluted sample is further diluted. The diluted sample is reacted for a predetermined time in the reaction chamber 13 in this state, whereby the first measurement sample in which the red blood cells in the blood sample are hemolyzed and the white blood cells and the nucleated red blood cells are stained is obtained.

The first measurement sample is sent to the white blood cell detecting part along with the sheath solution (Cell pack (II) manufactured by Sysmex Co.) by a constant-flow syringe (not shown), and measured in the white blood cell detecting part through the flow cytometry method.

Figure 5:
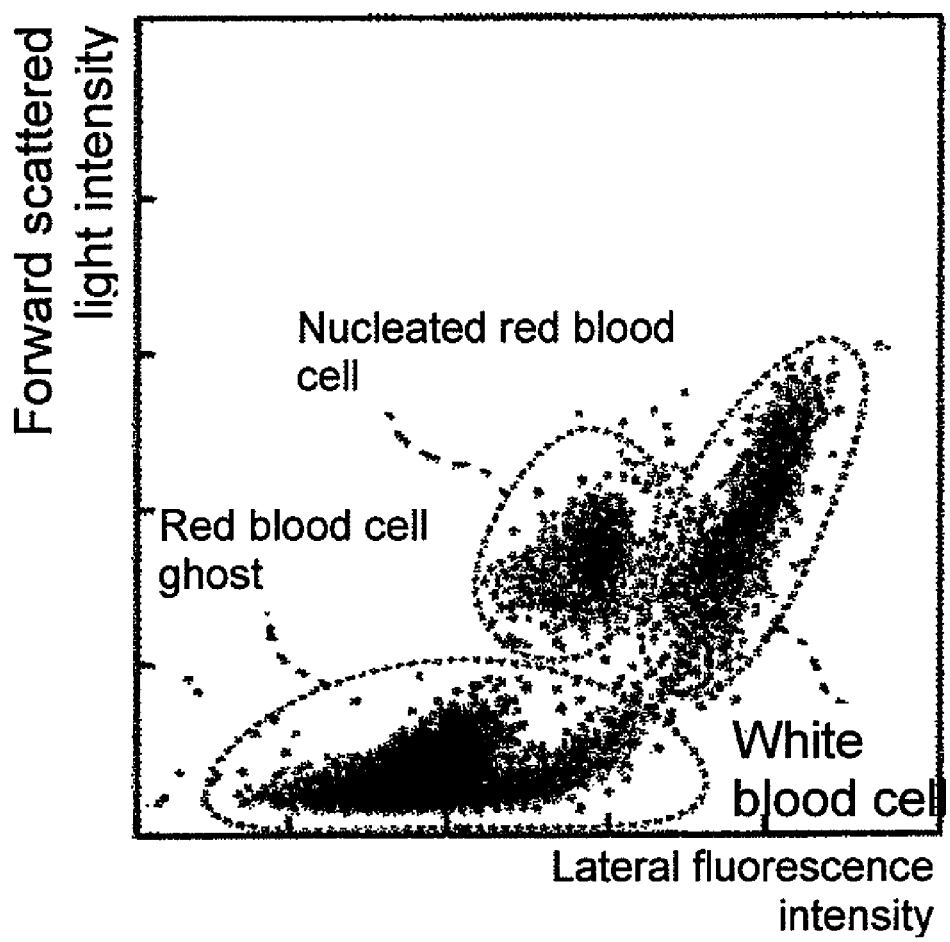
FIG. 5 shows a NRBC scattergram.

In the case of the first measurement, the distribution map creating part 64 generates a two-dimensional scattergram (particle distribution map) shown in FIG. 5 as the first measurement result with the forward scattered light intensity and the lateral fluorescence intensity obtained from the forward scattered signal and the lateral fluorescence signal output from the white blood cell detecting part as characteristic parameters.

The scattergram (hereinafter referred to NRBC scattergram) is drawn with the lateral fluorescence intensity on the X axis and the forward scattered light intensity on the Y axis, and "red blood cell ghost particle group", "nucleated red blood cell particle group", and "white blood cell particle group" appear when the nucleated red blood cell is contained in the blood sample. These particle groups are recognized by processing the NRBC scattergram with the data processing unit 3. The data processing unit 3 performs the nucleated red blood cells classification (NRBC classification), which is the first classification, and counts the nucleated red blood cells.

The second measurement (DIFF measurement) will now be described using FIG. 4.

In the case of the DIFF measurement, a second measurement sample in which a second reagent for the second measurement (DIFF measurement) is mixed with the blood sample is prepared, and the second measurement sample is measured by the white blood cell detecting part.

In FIG. 4, a second aliquot of the three aliquot, is diluted with a predetermined amount of hemolyzing agent (Stromatolyser 4DL manufactured by Sysmex Co.) serving as second reagent in the sampling valve 12, and conveyed to a reaction chamber 14 as diluted sample. A predetermined amount of stain solution (Stromatolyser 4DS manufactured by Sysmex Co.) serving as another second reagent is supplied to the reaction chamber 14, and the diluted sample is further diluted. The diluted sample is reacted for a predetermined time in the reaction chamber 14 in this state, whereby the second measurement sample in which the red blood cells in the blood sample are hemolyzed and the white blood cells are stained is obtained.

The second measurement sample is sent to the white blood cell detecting part along with the sheath solution (Cell pack (II) manufactured by Sysmex Co.) by a constant-flow syringe (not shown), and measured in the white blood cell detecting part through the flow cytometry method.

Figure 6:
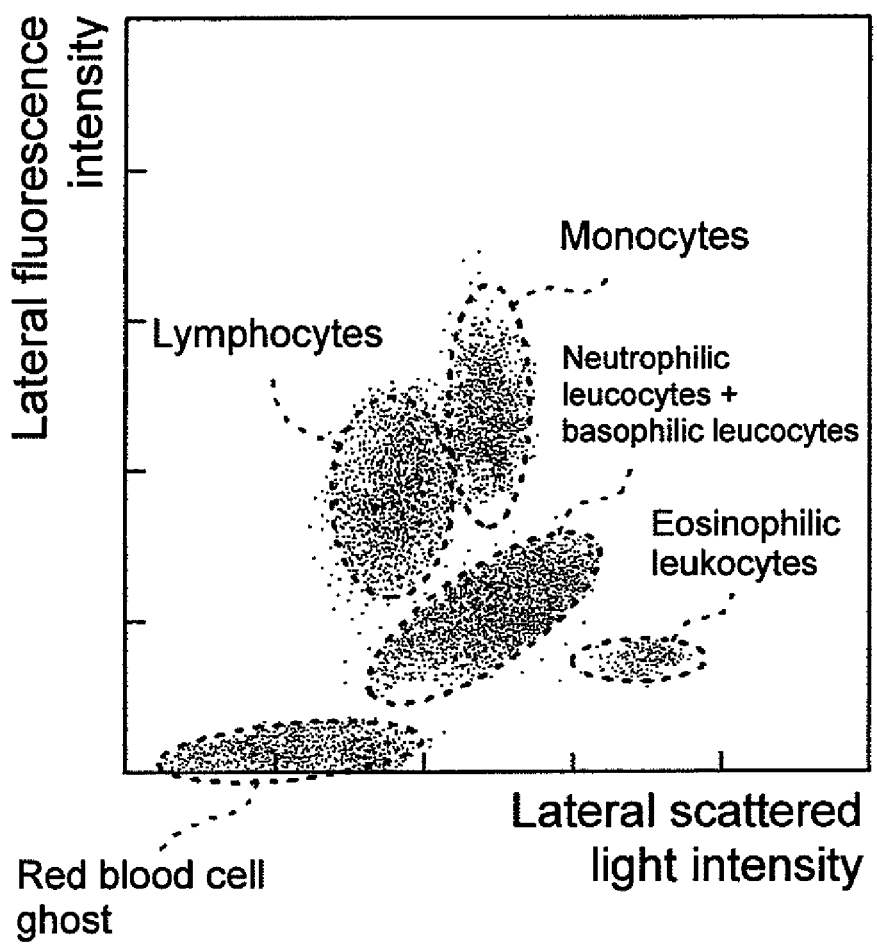
FIG. 6 shows a 4DIFF scattergram.

In the case of the second measurement, the distribution map creating part 64 generates a two-dimensional scattergram (particle distribution map) shown in FIG. 6 as the second measurement result with the lateral scattered light intensity and the lateral fluorescence intensity obtained from the lateral scattered signal and the lateral fluorescence signal output from the white blood cell detecting part as characteristic parameters.

The scattergram (hereinafter referred to DIFF scattergram) is drawn with the lateral scattered light intensity on the X axis and the lateral fluorescence intensity on the Y axis, and normally, "red blood cell ghost particle group", "lymphocytes particle group", "monocytes particle group", "neutrophilic leucocytes+basophilic leucocytes particle group" and "eosinophilic leukocytes particle group" appear. These particle groups are recognized by processing the DIFF scattergram with the data processing unit 3. The data processing unit 3 performs the white blood cells classification (DIFF classification), which is the second classification, and counts each classified white blood cells.

The hemolyzing agent (Stromatolyser 4DL manufactured by Sysmex Co.) serving as the second reagent has a relatively suppressed hemolyzing ability. The hemolyzing agent hemolyzes and contracts not only the red blood cells but also the white blood cells. When the white blood cells are hemolyzed in excess, classification of white blood cells becomes difficult, and thus the white blood cells are hemolyzed in a relatively gradual manner to suppress contraction of the white blood cells in DIFF in which the white blood cells are classified in a relatively fine manner.

The third measurement (WBC/BASO measurement) will now be described using FIG. 4.

In the case of the WBC/BASO measurement, a third measurement sample in which a third reagent for the third measurement (WBC/BASO measurement) is mixed with the blood sample is prepared, and the third measurement sample is measured by the white blood cell detecting part.

In FIG. 4, a third aliquot of the three aliquots is diluted with a predetermined amount of hemolyzing agent (Stromatolyser FB(II) manufactured by Sysmex Co.) serving as third reagent in the sampling valve 12, and conveyed to a reaction chamber 15 as diluted sample. The diluted sample is reacted for a predetermined time in the reaction chamber 15 in this state, whereby the third measurement sample in which the red blood cells in the blood sample are hemolyzed is obtained.

The third measurement sample is sent to the white blood cell detecting part along with the sheath solution (Cell pack (II) manufactured by Sysmex Co.) by a constant-flow syringe (not shown), and measured in the white blood cell detecting part through the flow cytometry method.

Figure 7:
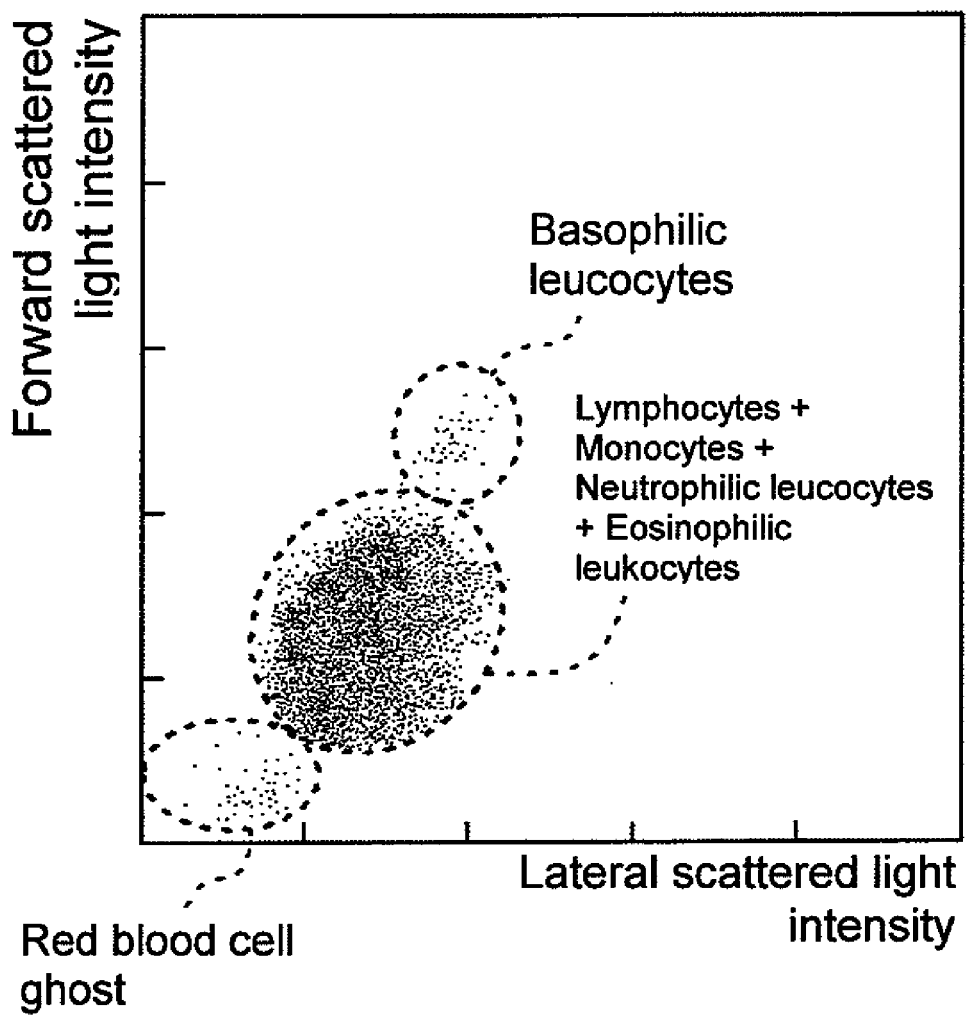
FIG. 7 shows a WBC/BASO scattergram.

In the case of the third measurement, the distribution map creating part 64 generates a two-dimensional scattergram (particle distribution map) shown in FIG. 7 as the third measurement result with the lateral scattered light intensity and the forward scattered light intensity obtained from the lateral scattered signal and the forward scattered light signal output from the white blood cell detecting part as characteristic parameters.

The scattergram (hereinafter referred to WBC/BASO scattergram) is drawn with the lateral scattered light intensity on the X axis and the forward scattered light intensity on the Y axis, and normally, "red blood cell ghost particle group", "basophilic leucocytes particle group", and "other white blood cells (lymphocytes, monocytes, neutrophilic leucocytes and eosinophilic leukocytes) particle group" appear. These particle groups are recognized by processing the WBC/BASO scattergram with the data processing unit 3. The data processing unit 3 performs classification of white blood cells (WBC/BASO classification), which is a third classification, and counts each classified white blood cells.

The hemolyzing agent (Stromatolyser FB(II) 4DL manufactured by Sysmex Co.) serving as the third reagent has a relatively higher hemolyzing ability than the hemolyzing agent (Stromatolyser 4DL) serving as the second reagent. In the third measurement (WBC/BASO), fine classification of white blood cells is not performed. Thus, even if the white blood cells are contracted to a certain extent by the hemolyzing agent, the white blood cells can be reliably counted by reliably hemolyzing the red blood cells with the hemolyzing agent. The number of white blood cells can be obtained while suppressing the influence caused by a change with time in the white blood cells after collecting blood.

Figure 8:
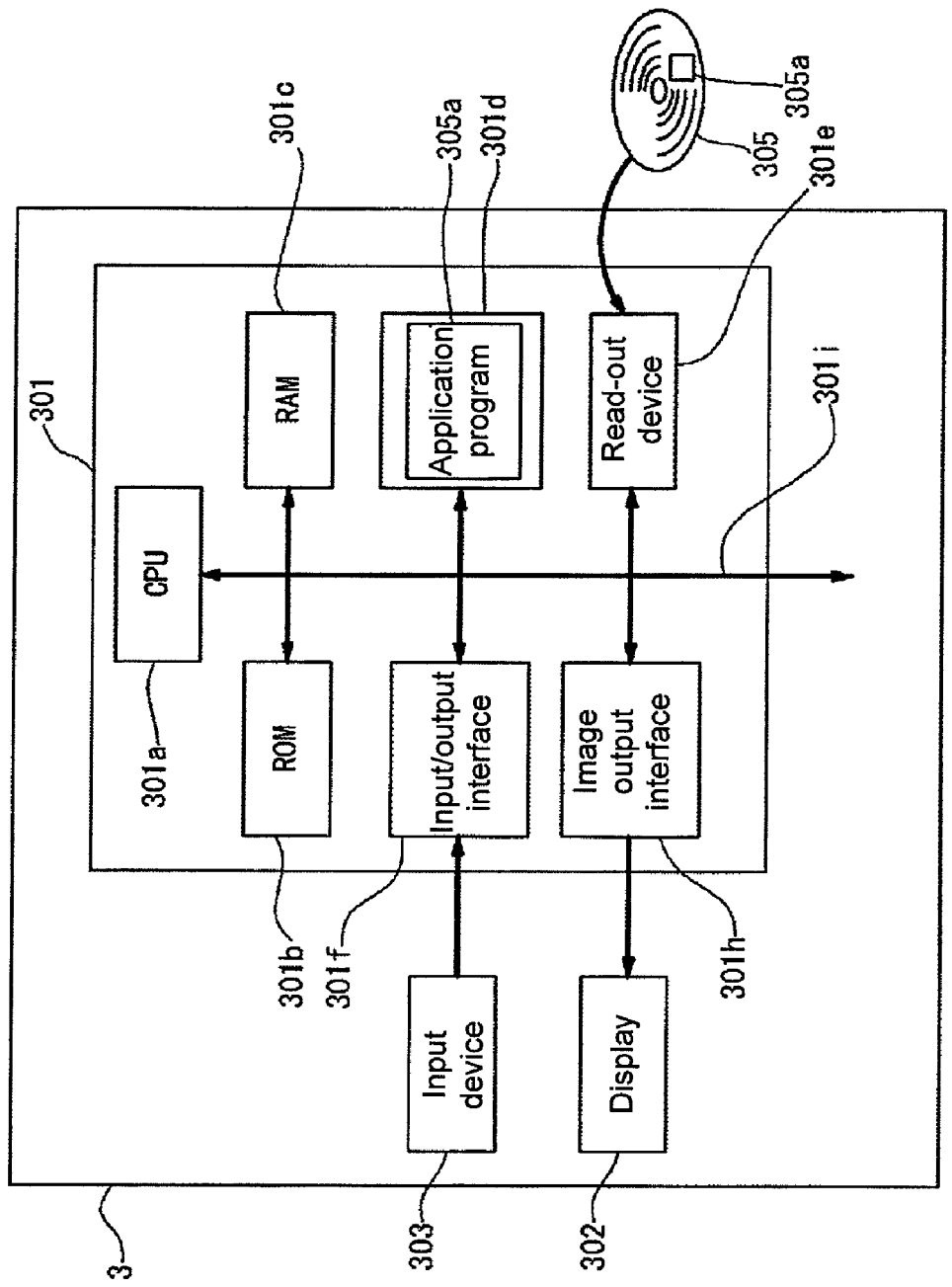
FIG. 8 is a functional block diagram of a data processing unit.

The microcomputer 6 of the measuring unit 2 sends the first, second, and third measurement results to the data processing unit 3. As shown in FIG. 8, the data processing unit 3 is configured by a computer, which is mainly configured by a main body 301, a display 302, and an input device 303. The main body 301 is mainly configured by CPU 301a, ROM 301b, RAM 301c, hard disc 301d, read-out device 301e, input/output interface 301f, and image output interface 301h, where the CPU 301a, ROM 301b, the RAM 301c, hard disc 301d, read-out device 301e, input/output interface 301f, and image output interface 301h are connected by a bus 301i so as to communicate data.

The CPU 301a is capable of executing the computer program stored in the ROM 301b and the computer program loaded in the RAM 301c. When the CPU 301a executes an application program 305a, to be hereinafter described, the computer functions as the data processing unit 3.

The ROM 301b is configured by mask ROM, PROM, EPROM, EEPROM, and the like, and is recorded with the computer program to be executed by the CPU 301a, data used for the same, and the like.

The RAM 301c is configured by SRAM, DRAM, or the like. The RAM 301c is used to read out the computer program recorded on the ROM 301b and the hard disc 301d. When executing such computer program, the RAM 301c is used as a work region of the CPU 301a.

The hard disc 301d is installed with various computer programs for the CPU 301a to execute such as operating system and application program, and data used in execution of the computer programs. The application program 305a to be hereinafter described is also installed in the hard disc 301d.

The read-out device 301e is configured by flexible disc drive, CD-ROM drive, DVD-ROM, or the like, and reads computer program or data recorded on a portable recording medium 305. The application program 350a for the computer to realize a predetermined function is stored in the portable recording medium 305, and the computer serving as the data processing unit 3 is able to read out the application program 305a from the portable recording medium 305 and install the application program 305a in the hard disc 301d.

The application program 305a is not only provided by the portable recording medium 305, but also provided through the electric telecommunication line (wired or wireless) from the external equipment communicably connected to the data processing unit 3 by the electric telecommunication line. For instance, the data processing unit 3 may download, through the Internet, the application program 305a stored in the hard disc of the server computer connected with the data processing unit 3 through the Internet, and install the same in the hard disc 301d.

The operating system that provides graphical user interface environment such as Windows (Registered trademark) manufactured and sold by US Microsoft Co., Ltd. is installed in the hard disc 301d. In the following description, the application program 305a according to the present embodiment operates on the operating system.

The input/output interface 301f is configured by serial interface such as USB, IEEE1394, RS-232C; parallel interface such as SCSI, IDE, IEEE1284; analog interface including D/A converter, A/D converter and the like. The input device 303 including keyboard and mouse is connected to the input/output interface 301f, so that the data can be input to the data processing unit 3 when the user uses the input device 303.

The image output interface 301h is connected to the display 302 configured by LCD, CRT, or the like, and outputs an image signal corresponding to the image data provided from the CPU 301a to the display 302. The display 302 displays the image (screen) according to the input image signal.

Figure 9:
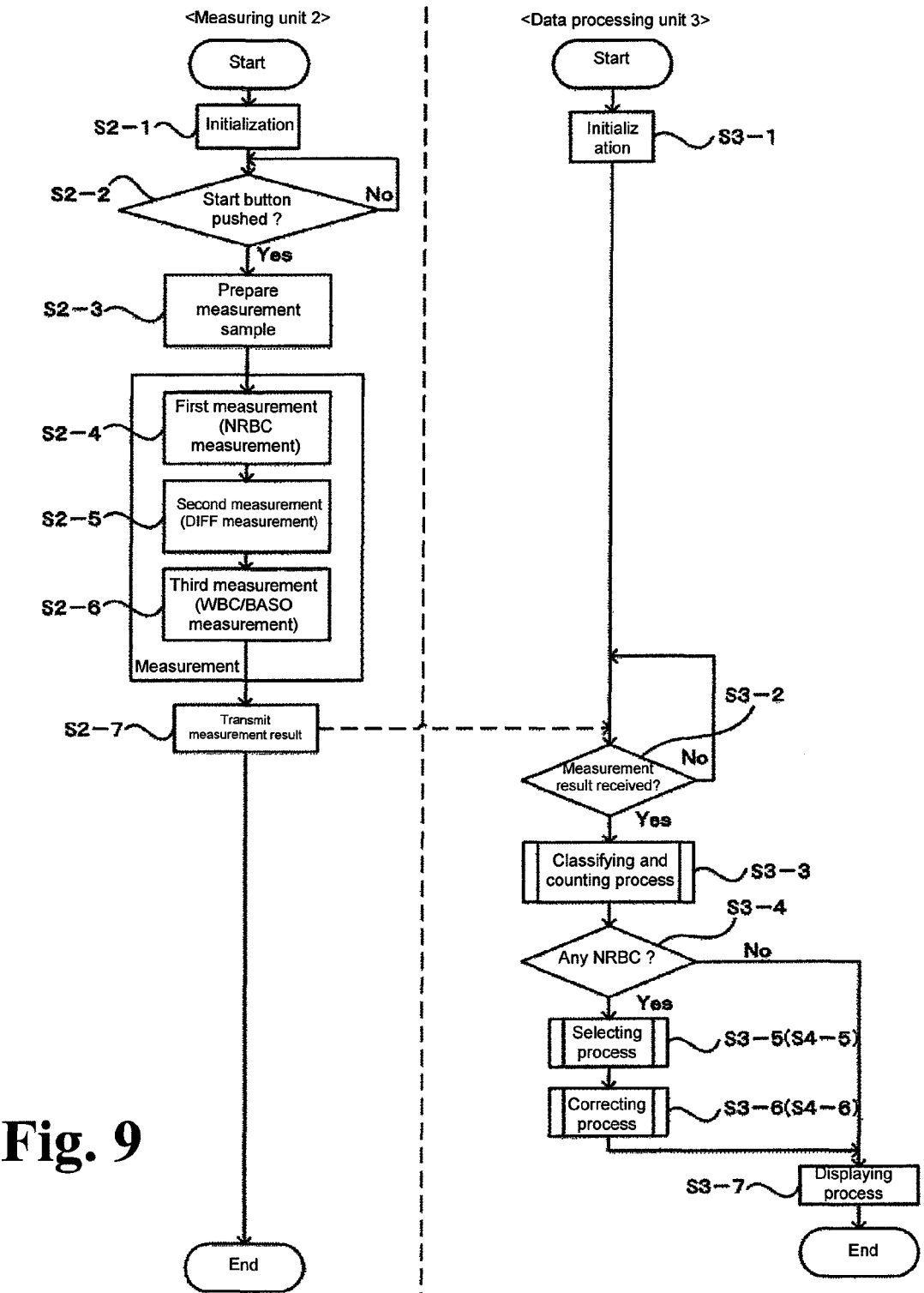
FIG. 9 is a flowchart of processes by the measuring unit and the data processing unit.

The flow of process by the measuring unit 2 and the data processing unit 3 will now be described using FIG. 9. FIG. 9 is a flowchart showing a flow of the operation of the measuring unit 2 and the data processing unit 3 according to the present embodiment. First, when the power of the measuring unit 2 and the data processing unit 3 is turned ON by the operation of the user, initialization of each mechanism section of the measuring unit 2, and initialization of the computer program etc. stored in the data processing unit 3 are performed (step S2-1, S3-1).

Subsequently, after input of the sample number, setting of operation conditions, and the like are made by the operation of the user in the measuring unit 2, the measuring unit 2 determines whether or not a start button (not shown) is pushed (step S2-2).

If the start button is pushed, the measuring unit 2 prepares the first to the third measurement samples (step S2-3). The preparation of the first to the third measurement samples in step S2-3 is performed in parallel.

The first measurement (NRBC measurement) (step S2-4), the second measurement (4DIFF measurement) (step S2-5), and the third measurement (WBC/BASO measurement) (step S2-6) are sequentially performed by the white blood cell measuring part of the measuring unit 2. Here, a configuration in which the first to the third measurements are sequentially performed by one white blood cell detecting part has been described, but is not limited thereto, and a configuration in which a detecting part for performing the first measurement, a detecting part for performing the second measurement and a detecting part for performing the third measurement are respectively arranged, and the first to the third measurements are performed in parallel may be adopted.

The measuring unit 2 then transmits the measurement results (first to third measurement results) obtained in the first to the third measurements to the data processing unit 3 (step S2-7).

The data processing unit 3 determines whether or not the first to the third measurement results are received from the measuring unit 2 (step S3-2), and executes the classification and counting processing described below when determined that the measurement results are received.

[Classifying and Counting Process]

Figure 10:
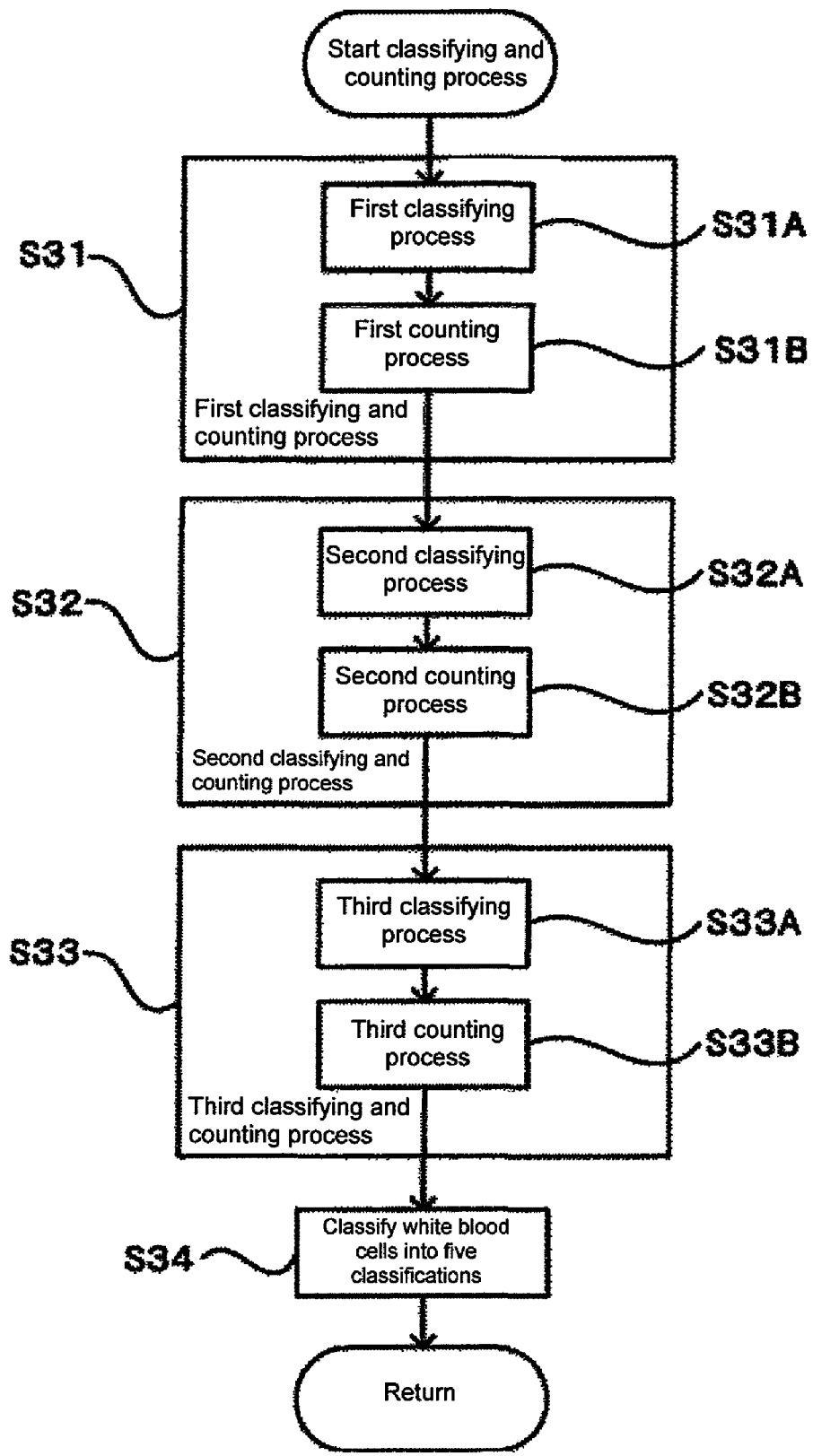
FIG. 10 is a flowchart showing details of processing procedures of a classifying and counting process.

The CPU 301a of the data processing unit 3 executes the classifying and counting process of particles contained in the measurement sample based on the first to the third measurement results (step S3-3). Specifically, as shown in FIG. 10, the CPU 301a executes a first classifying and counting process for classifying and counting the nucleated red blood cells with respect to the NRBC measurement (first measurement) result (step S31). The CPU 301a executes second and third classifying and counting processes for classifying and counting the white blood cells with respect to the DIFF measurement (second measurement) and the WBC/BASO measurement (third measurement) results (steps S32, S33). The first classifying and counting process will be described below.

(First Classifying and Counting Process)

In the first classifying and counting process, the CPU 301a of the data processing unit 3 first executes the first classifying process (step S31A). In the first classifying process, nucleated red blood cell particle group (cluster), white blood cell cluster, and red blood cell ghost cluster are classified on the NRBC scattergram. In the first classifying process of the present embodiment, the degree of attribution on each cluster of each particle is obtained from the distance between each particle plotted on the scattergram and the barycentric position of each cluster. Each particle is then assigned to each cluster depending on the degree of attribution. Such particle classifying method is disclosed in detail in U.S. Pat. No. 5,555,196. Accordingly, as shown in FIG. 5, a boundary for distinguishing the nucleated red blood cell cluster and the other regions, a boundary for distinguishing the white blood cell cluster and the other regions, and a boundary for distinguishing the red blood cell ghost cluster and the other regions are formed on the NRBC scattergram. The particles existing within such boundaries are recognized by the CPU 301a as particles belonging to a cluster.

The CPU 301a of the data processing unit 3 then executes the first counting process (step S31B). In the first counting process, the particles of the nucleated red blood cell cluster classified in the first classifying process are counted.

(Second Classifying and Counting Process)

In the second classifying and counting process, the CPU 301a of the data processing unit 3 first executes the second classifying process (step S32A). In the second classifying process, lymphocytes cluster, monocytes cluster, neutrophilic leucocytes+basophilic leucocytes cluster, eosinophilic leukocytes cluster, and red blood cells ghost cluster are classified on the DIFF scattergram. The algorithm of the second classifying process of step 32B is similar to the first classifying process of step S31A described above, and thus the description thereof will be omitted. Accordingly, as shown in FIG. 6, a boundary for distinguishing the lymphocytes cluster and the other regions, a boundary for distinguishing the monocytes cluster and the other regions, a boundary for distinguishing neutrophilic leucocytes+basophilic leucocytes cluster and the other regions, a boundary for distinguishing eosinophilic leukocytes cluster and the other regions, and a boundary for distinguishing red blood cells ghost cluster and the other regions are generated on the DIFF scattergram. The particles existing within such boundaries are recognized by the CPU 301a as particles belonging to a cluster.

The CPU 301a of the data processing unit 3 then executes the second counting process (step S32B). In the second counting process, the particles of the four clusters of white blood cells and the particles of the red blood cell ghost cluster classified in the second classifying process are counted. Accordingly, each number of blood cells of the lymphocytes, monocytes, neutrophilic leucocytes+basophilic leucocytes, and eosinophilic leukocytes, and the particle number of the red blood cell ghost are obtained.

(Third Classifying and Counting Process)

In the third classifying and counting process, the CPU 301a of the data processing unit 3 first executes the third classifying process (step S33A). In the third classifying process, basophilic leucocytes cluster, white blood cell cluster other than basophilic leucocytes, and red blood cell ghost cluster are classified on the WBC/BASO scattergram. The algorithm of the third classifying process of step 33A is similar to the first classifying process of step S31A described above, and thus the description thereof will be omitted. Accordingly, as shown in FIG. 7, a boundary for distinguishing the basophilic leucocytes cluster and the other regions, a boundary for distinguishing white blood cells cluster other than basophilic leucocytes and the other regions, and a boundary for distinguishing the red blood cells ghost cluster and the other regions are generated on the WBC/BASO scattergram. The particles existing within such boundaries are recognized by the CPU 301a as particles belonging to a cluster.

The CPU 301a of the data processing unit 3 then executes the third counting process (step S33B). In the third counting process, the particles of the two clusters of white blood cells classified in the third classifying process are counted. Accordingly, each number of blood cells of the basophilic leucocytes and the white blood cells other than the basophilic leucocytes. In the present embodiment, the total number of white blood cells contained in the blood sample is obtained by calculating the sum of each particle number of the basophilic leucocytes cluster and the white blood cell cluster other than the basophilic leucocytes classified on the WBC/BASO scattergram.

(Classification of White Blood Cells into Five Classifications)

The CPU 301a of the data processing unit 3 classifies the white blood cells contained in the blood sample into five classifications based on the result of classifying the white blood cells into four and counting the same by the second classifying and counting process, and the result of classifying the white blood cells into two and counting the same by the third classifying and counting process (step S34). Specifically, the CPU 301a subtracts "number of blood cells of basophilic leucocytes" obtained by the third classifying and counting process from the "number of blood cells of neutrophilic leucocytes+basophilic leukocytes" obtained by the second classifying and counting process to obtain the number of blood cells of the neutrophilic leucocytes and the number of blood cells of the basophilic leucocytes. The white blood cells are thus classified into five classifications (lymphocytes, monocytes, neutrophilic leucocytes, basophilic leucocytes, and eosinophilic leukocytes), and the number of blood cells of each classified item is obtained.

[Determining Process]

The CPU 301a of the data processing unit 3 determines whether or not the nucleated red blood cells are contained in the measured blood sample based on the counted result by the first classifying and counting process (step S3-4).

In the analyzer 1 according to the present embodiment, the nucleated red blood cells appear in the distribution region of the white blood cells other than the basophilic leucocytes on the WBC/BASO scattergram when the blood sample containing the nucleated red blood cells is measured. Since the sum of each particle number of the basophilic leucocytes cluster and the white blood cell cluster other than the basophilic leucocytes classified on the WBC/BASO scattergram is assumed as the total number of white blood cells in the present embodiment, the total number of white blood cells obtained by the third classifying and counting process contains error caused by the nucleated red blood cells when the blood sample contains the nucleated red blood cells.

Thus, the total number of white blood cells obtained by the third classifying and counting process must be corrected when the blood sample containing the nucleated red blood cells is measured.

Figure 11:
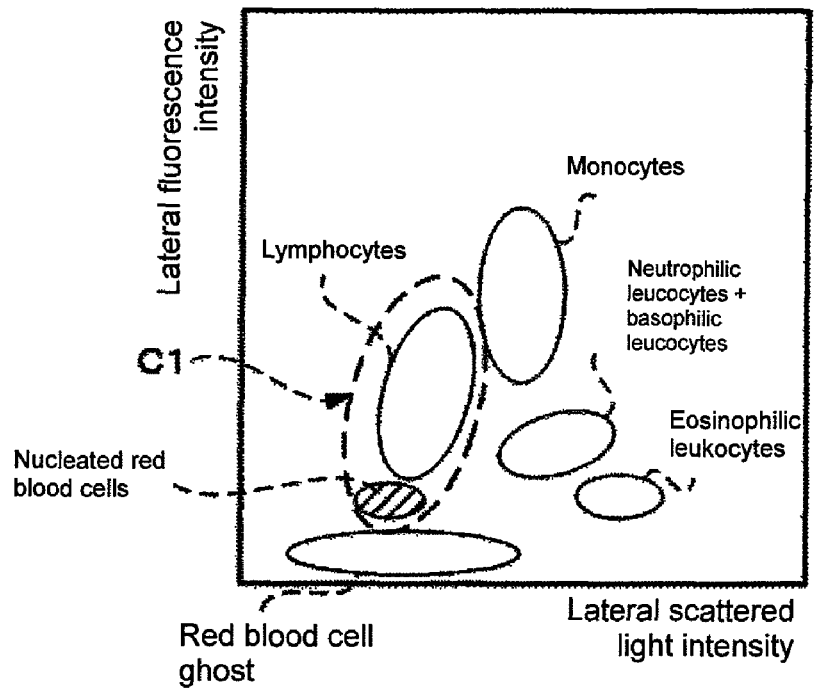
FIG. 11 is an explanatory view showing classification of nucleated red blood cells as lymphocytes on the 4DIFF scattergram.
Figure 12:
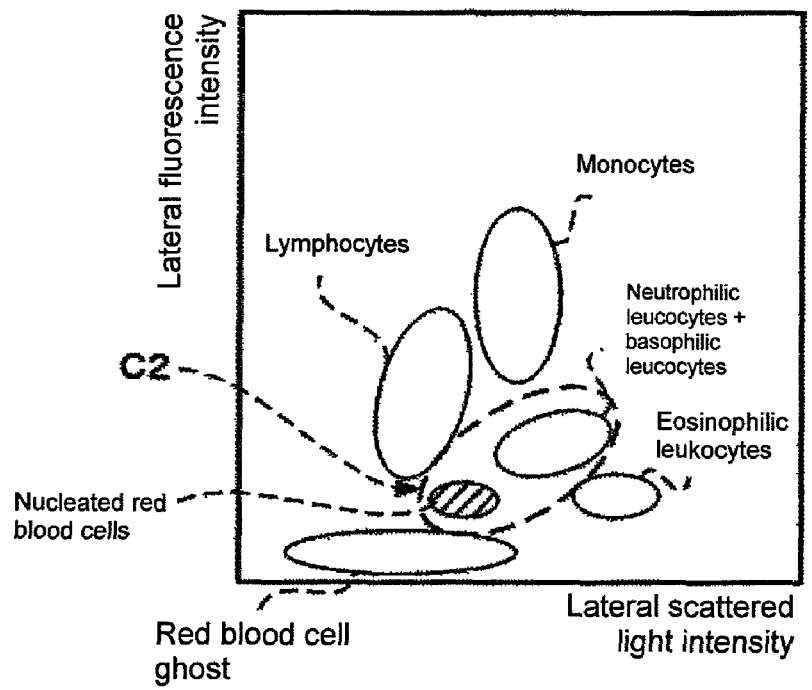
FIG. 12 is an explanatory view showing classification of nucleated red blood cells as neutrophilic leucocytes on the 4DIFF scattergram.

Furthermore, when the blood sample containing the nucleated red blood cells is measured, the result of classification of white blood cells into five classifications obtained as above sometimes contains error caused by the nucleated red blood cells. For instance, as shown in FIG. 11, in the case of the blood sample in which the nucleated red blood cells appear at the lower left of the distribution region of the lymphocytes on the DIFF scattergram, the nucleated red blood cells are classified as the lymphocytes cluster C1 as a result of the second classifying and counting process. Moreover, as shown in FIG. 12, in the case of the blood sample in which the nucleated red blood cells appear at the lower left of the distribution region of the neutrophilic leucocytes on the DIFF scattergram, the nucleated red blood cells are classified as the neutrophilic leucocytes cluster C2. Although not shown, the nucleated red blood cells are sometimes classified as red blood cell ghost cluster.

Thus, when the blood sample containing the nucleated red blood cells is measured, the number of lymphocytes or the number of neutrophilic leucocytes obtained by classification of white blood cells into five classifications (see FIG. 10) sometimes need to be corrected.

When determining that the nucleated red blood cells are contained in the blood sample in step S3-4, the CPU 301a of the data processing unit 3 executes a selecting process in step S3-5 to be hereinafter described. When determining that the nucleated red blood cells are not contained in the blood sample in step S3-4, the CPU 301a of the data processing unit 3 displays the classification result obtained by classification of white blood cells into five classifications and the total number of white blood cells obtained by the third classifying and counting process on the display 302 (step S3-7). In this case, the classification result obtained by classification of white blood cells into five classifications and the total number of white blood cells are displayed without correcting.

[Selecting Process]

Figure 13:
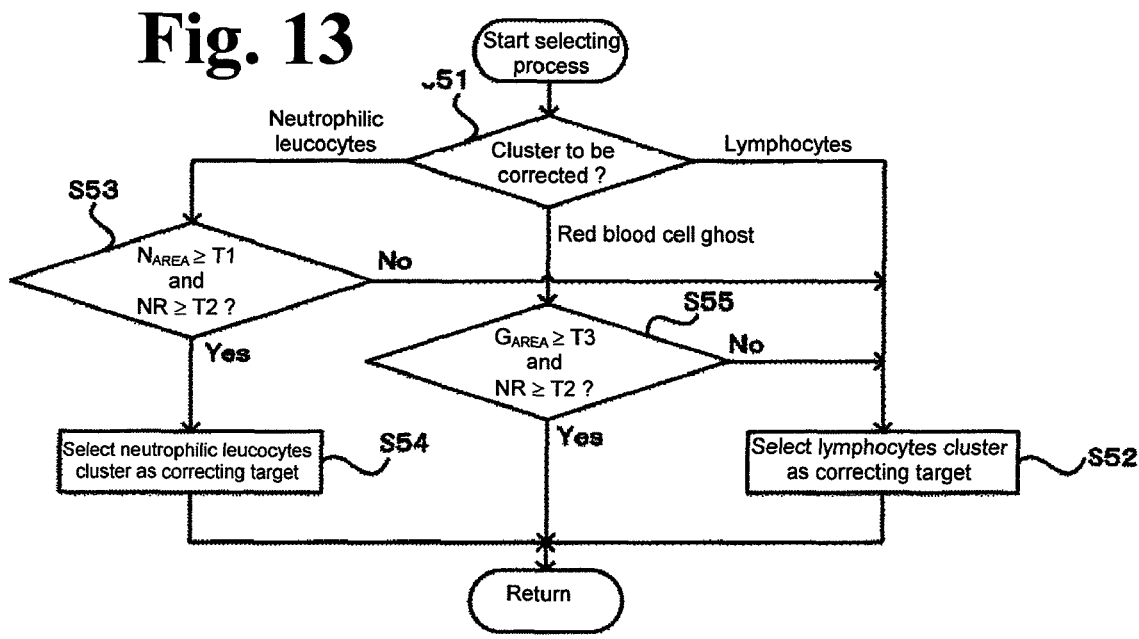
FIG. 13 is a flowchart of a selecting process in the data processing unit.

FIG. 13 shows a procedure of the selecting process by the CPU 301a of the data processing unit 3. In the selecting process, the CPU 301a selects a cluster to be performed with a correction (NRBC correction) of subtracting the number of nucleated red blood cells from the lymphocytes cluster and the neutrophilic leucocytes cluster on the DIFF scattergram (step S3-5). The selecting process will be described in detail below.

Figure 14:
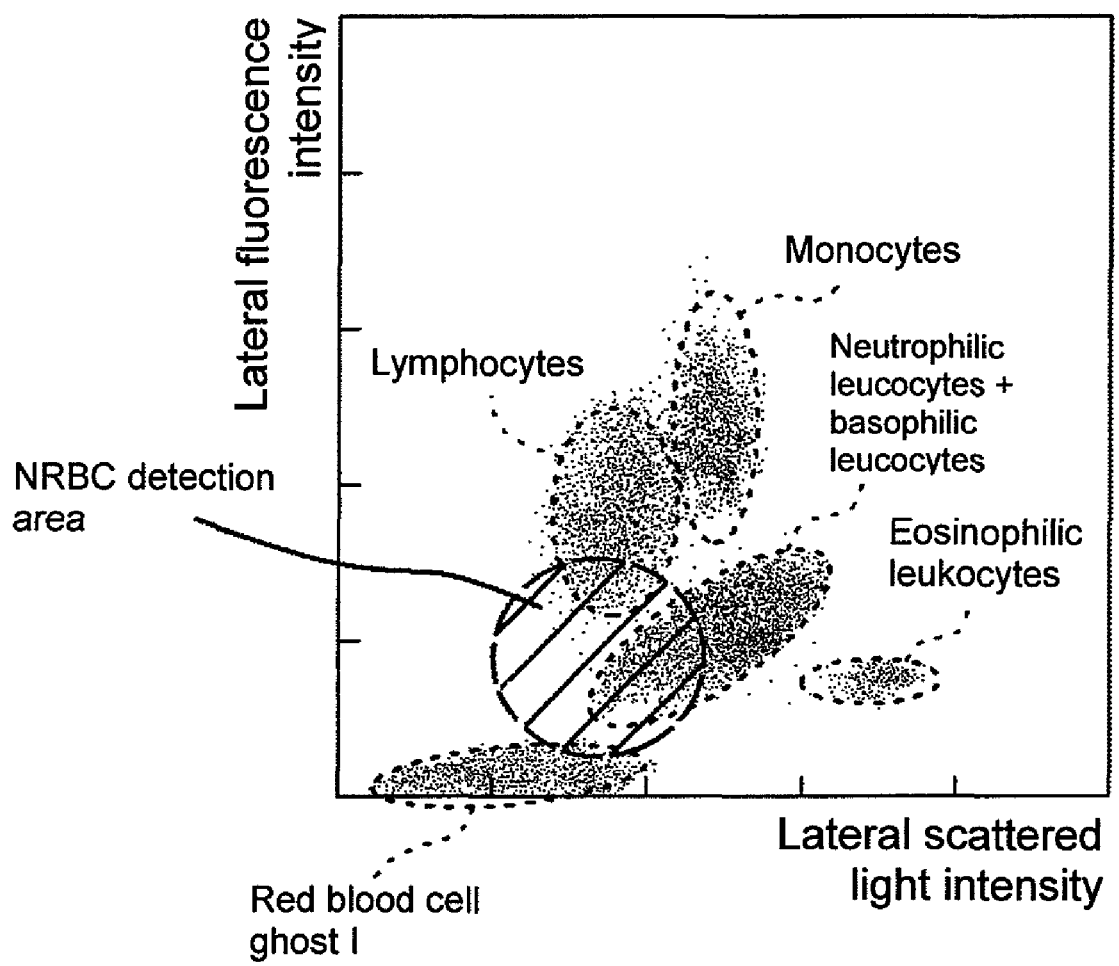
FIG. 14 is an explanatory view for selecting a particle group on the scattergram, particle number of the particle group being corrected.

In the present embodiment, as shown in FIG. 14, a specific region (shaded part) on the DIFF scattergram is set in advance as a nucleated red blood cell (NRBC) detection area. The NRBC detection area is an area where the nucleated red blood cells appear in great numbers on the DIFF scattergram when the blood sample containing the nucleated red blood cells is measured. Therefore, the nucleated red blood cells are assumed to be contained in the cluster of particles appearing in the NRBC detection area. Thus, in the selecting process of the present embodiment, the CPU 301a first determines which of the lymphocytes cluster, the neutrophilic leucocytes cluster, or the red blood cell ghost cluster particles appear the most in the NRBC detection area (step S51). The cluster which particles appear the most in the NRBC detection area is referred as "correction candidate cluster" below.

If the correction candidate cluster is the lymphocytes cluster, the CPU 301a selects the lymphocytes cluster as the cluster to be NRBC corrected (step S52), and returns the process.

If the correction candidate cluster is the neutrophilic leucocytes cluster, the CPU 301a determines whether or not the particle number $N_{AREA}$ of the neutrophilic leucocytes in the NRBC detection area is greater than or equal to a predetermined number (T1), and whether or not the number of nucleated red blood cells NR obtained by the first classifying and counting process is greater than or equal to a predetermined number (T2), that is, whether the following equations (1) and (2) are both met (step S53).

$$N_{AREA} \geq T1 \tag{1}$$

$$NR \geq T2 \tag{2}$$

When both equations (1) and (2) are met, the CPU 301a selects the neutrophilic leucocytes cluster as the cluster to be NRBC corrected (step S54), and returns the process. When at least one of the equations (1) and (2) is met, the CPU 301a selects the lymphocytes cluster as the cluster to be NRBC corrected (step S52), and returns the process.

Furthermore, if the correction candidate cluster is the red blood cell ghost cluster, the CPU 301a determines whether the particle number $G_{AREA}$ of the red blood cell ghost in the NRBC detection area is greater than or equal to a predetermined number (T3), and whether or not the number of nucleated red blood cells NR obtained by the first classifying and counting process is greater than or equal to a predetermined number (T2), that is, whether the following equations (3) and (4) are both met (step S55).

$$G_{AREA} \geq T3 \tag{3}$$

$$NR \geq T2 \tag{4}$$

When both equations (3) and (4) are met, the CPU 301a does not select any cluster as the cluster to be NRBC corrected, and returns the process. When at least one of the equations (3) and (4) is met, the CPU 301a selects the lymphocytes cluster as the cluster to be NRBC corrected (step S52), and returns the process.

[Correcting Process]

Figure 15:
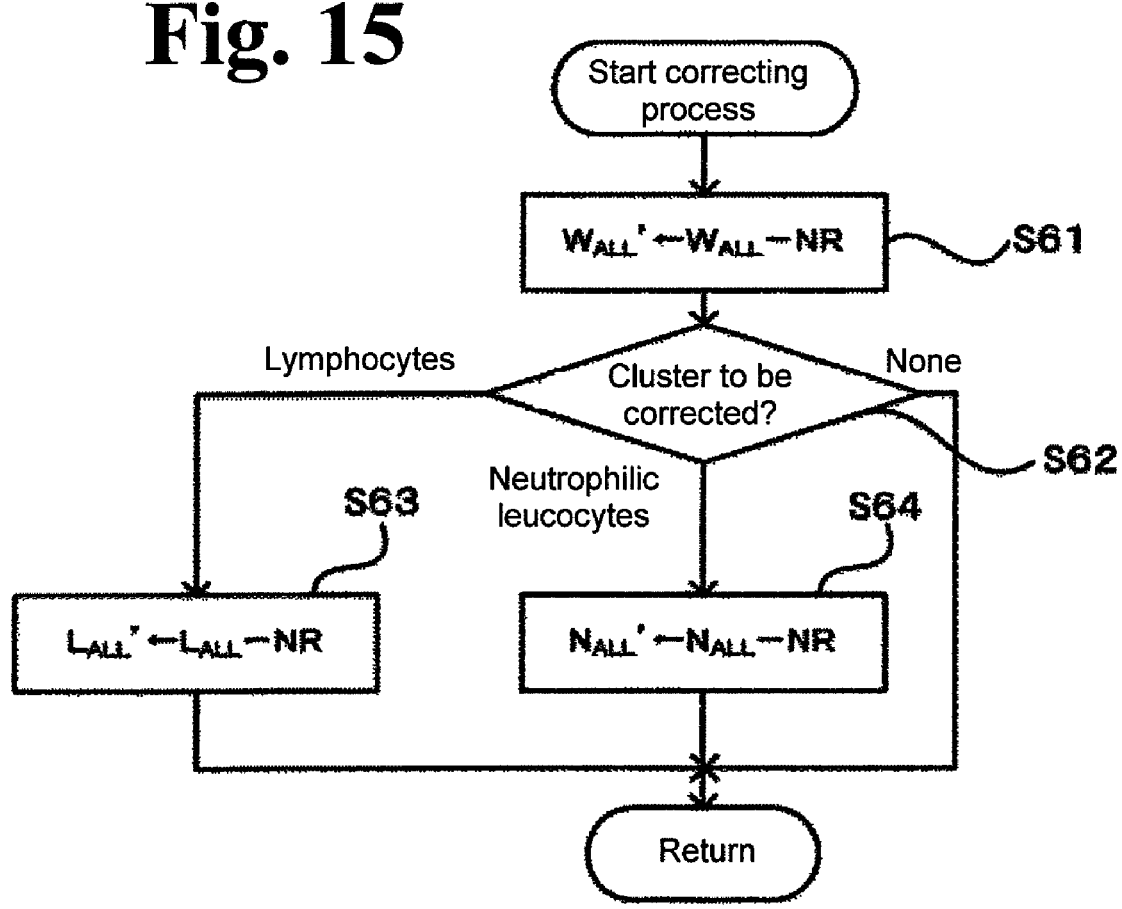
FIG. 15 is a flowchart of a correcting process in the data processing unit.

The CPU 301a of the data processing unit 3 corrects the total number of white blood cells obtained by the third classifying and counting process and the particle number of the cluster selected as the correcting target by the selecting process (NRBC correction) (step S3-6). FIG. 15 is a flowchart showing a procedure of the correcting process. The correcting process will be described in detail with reference to FIG. 15.

First, the CPU 301a subtracts the number of nucleated red blood cells NR obtained by the first classifying and counting process (NRBC classifying and counting process) from the total number of white blood cells $W_{ALL}$ obtained by the third classifying and counting process (step S61).

The CPU 301a then determines which cluster is selected as the correcting target or whether none of the cluster is selected as the cluster to be corrected (step S62). If the cluster to be corrected is the lymphocytes cluster, the CPU 301a subtracts the number of nucleated red blood cells NR obtained by the NRBC classifying and counting process from the number of lymphocytes (all particle numbers contained in the lymphocytes cluster) $L_{ALL}$ obtained by the five classifications of the white blood cells (see FIG. 10) (step S63), and returns the process. If the cluster to be corrected is the neutrophilic leucocytes cluster, the CPU 301a subtracts the number of nucleated red blood cells NR obtained by the NRBC classifying and counting process from the number of neutrophilic leucocytes $N_{ALL}$ obtained by the five classifications of the white blood cells (step S64), and returns the process. If the cluster to be corrected does not exist, the CPU 301a returns the process as it is.

[Displaying Process]

Figure 16:
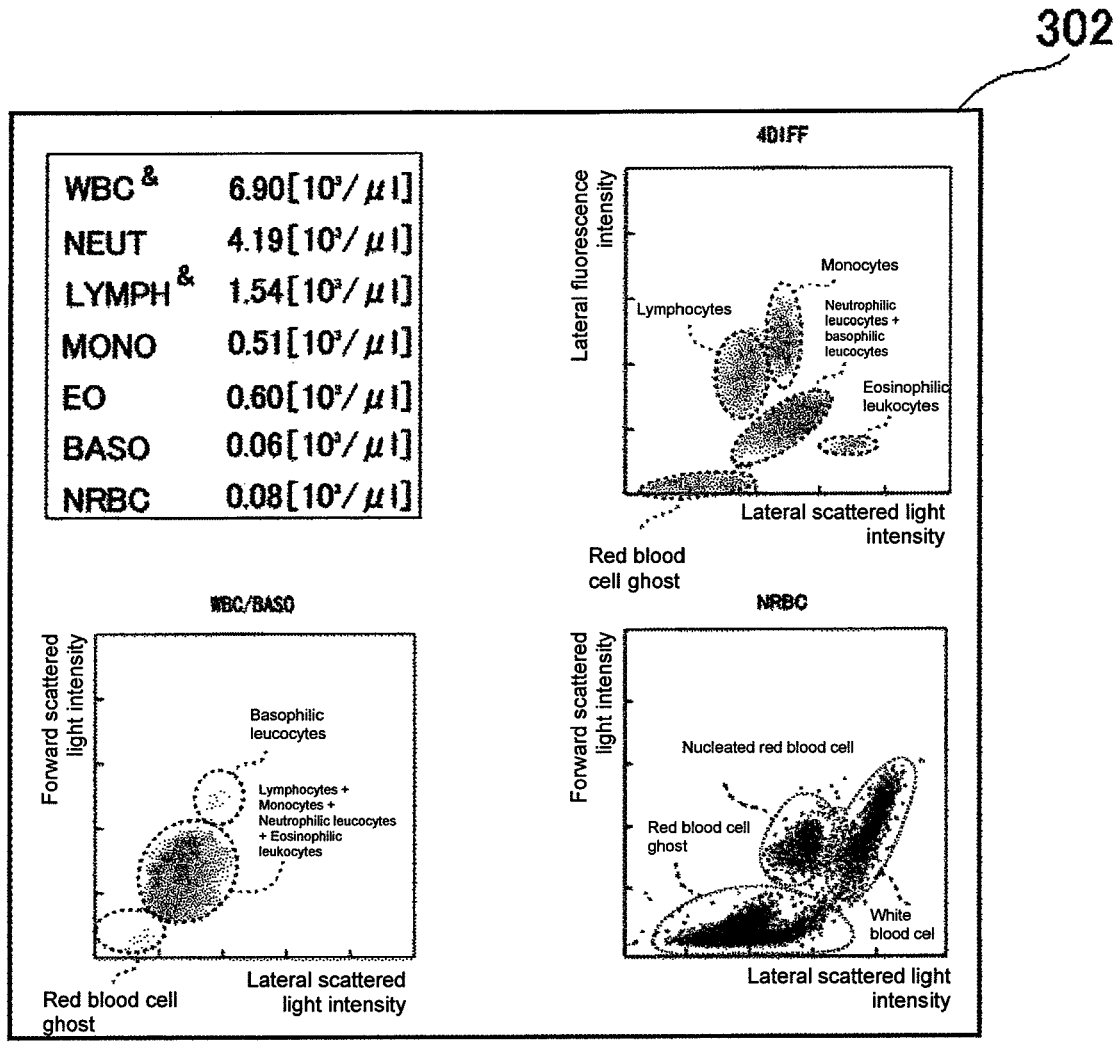
FIG. 16 is a display screen for displaying classification results.

The CPU 301a of the data processing unit 3 displays the analysis results obtained as above on the display 302 (step S3-7). Specifically, in the displaying process, the counting result of the total number of white blood cells (WBC), the counting result of the five types of white blood cells (NEUT, LYMPH, MONO, EO, BASO), the counting result of the nucleated red blood cells (NRBC), the WBC/BASO scattergram, the DIFF scattergram, and the NRBC scattergram are displayed, as shown in FIG. 16. If the particle number of the lymphocytes cluster and the total number of white blood cells are corrected by the correcting process, a & mark indicating that correction has been performed is denoted at the display position of the LYMPH (number of lymphocytes) and WBC (total number of white blood cells), as shown in FIG. 16. The user then is able to know that the particle number of the lymphocytes cluster and the total number of white blood cells are corrected based on the number of nucleated red blood cells. If the particle number of the neutrophilic leucocytes cluster and the total number of white blood cells are corrected by the correcting process, a & mark is denoted at the display position of the NEUT (neutrophilic leucocytes) and the WBC. The user then is able to know that the particle number of the neutrophilic leucocytes cluster and the total number of white blood cells are corrected based on the number of nucleated red blood cells. If the cluster to be corrected is not selected by the selecting process and only the total number of white blood cells is corrected based on the number of nucleated red blood cells, a & mark is denoted only at the display position of the WBC.

As described above, according to the blood analyzer 1 of the present embodiment, even if the specific kind of particle (nucleated red blood cell) is contained in one of the clusters of the plurality of types of particles (neutrophilic leucocytes, lymphocytes) different from the specific kind of particles, the cluster containing the specific kind of particles is selected as the correcting target and the particle number of the cluster to be corrected is corrected. The white blood cells thus can be classified and counted with satisfactory accuracy.

Figure 17:
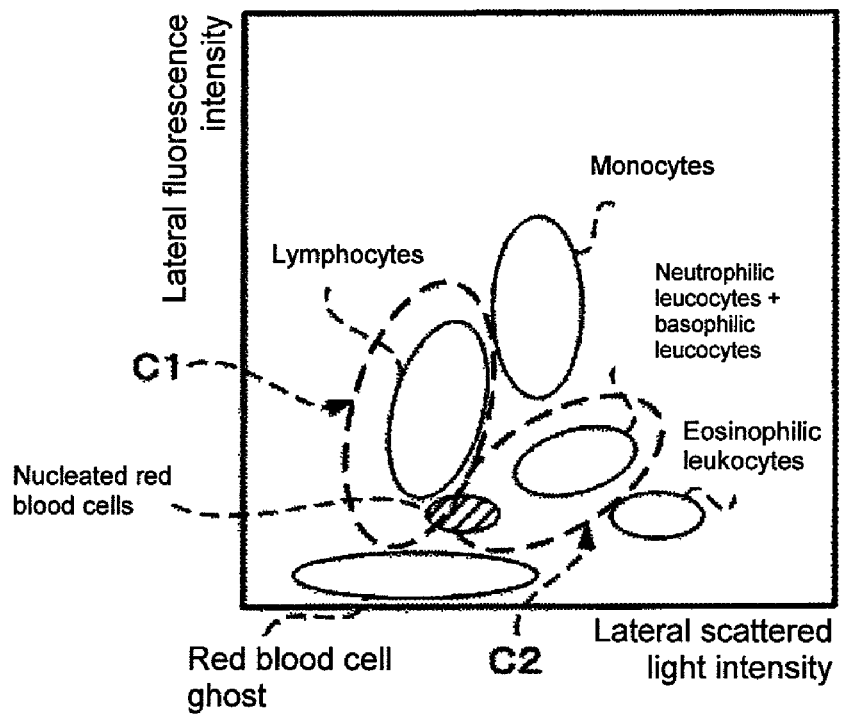
FIG. 17 is an explanatory view showing classification of one part of the nucleated red blood cells as lymphocytes, and other part of the nucleated red blood cells as neutrophilic leucocytes on the 4DIFF scattergram.

In the present embodiment, the NRBC correction of subtracting the number of nucleated red blood cells from the particle number of the cluster in which the particles appear the most in the NRBC detection area is performed, but the present embodiment is not limited thereto. A case where the nucleated red blood cells is divided and contained in a plurality of clusters on the DIFF scattergram can be assumed. As in the scattergram shown in FIG. 17, one part of the nucleated red blood cells are contained in the cluster C1 classified as lymphocytes, and another part of the nucleated red blood cells are contained in the cluster C2 classified as neutrophilic leucocytes. In such case, the degree of correction of each cluster C1, C2 is obtained, and the NRBC correction is performed on the particle number of each cluster C1, C2 according to such degree.

Figure 18:
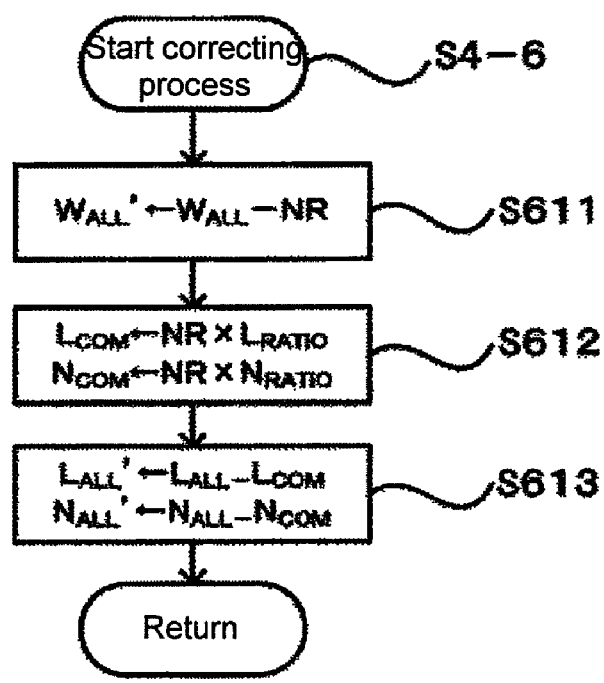
FIG. 18 is a flowchart showing a correcting process according to a variant.

FIG. 18 is a flowchart showing a procedure of the correcting process according to a variant. In the variant, the CPU 301a determines the degree of correction of the lymphocytes cluster and the degree of correction of the neutrophilic leucocytes cluster in the selecting process of step S4-5 shown in FIG. 9. Specifically, the CPU 301a calculates the ratio $L_{RATIO}$ of the particle number contained in the lymphocytes cluster, and the ratio $N_{RATIO}$ of the particle number contained in the neutrophilic leucocytes cluster in the particle number appearing in the NRBC detection area. In the correcting process S4-6, the CPU 301a first subtracts the number of nucleated red blood cells NR obtained in the NRBC classifying and counting process from the total number of white blood cells $W_{ALL}$ obtained in the third classifying and counting process (step S611) The CPU 301a calculates the lymphocytes number correction value $L_{COM}$ by multiplying the ratio $L_{RATIO}$ of the particle number of the lymphocytes to the number of nucleated red blood cells NR, and calculates the neutrophilic leucocytes number correction value $N_{COM}$ by multiplying the ratio $N_{RATIO}$ of the particle number of the neutrophilic leucocytes to the number of nucleated red blood cells NR (step S612). The CPU 301a subtracts the lymphocytes number correction value $L_{COM}$ from the number of lymphocytes $L_{ALL}$ obtained by classifying the white blood cells into five classifications (see FIG. 10), and subtracts the neutrophilic leucocytes number correction value $N_{COM}$ from the number of neutrophilic leucocytes $N_{ALL}$ obtained by classifying the white blood cells into five classifications (step S613), and returns the process. According to the above process, even if the nucleated red blood cells is divided and contained in the plurality of clusters on the DIFF scattergram, the particle number of each cluster can be corrected according to the degree of correction defined for every cluster.

In the present embodiment, the scattergram is created by the distribution map creating part 64 of the measuring unit 2, but the scattergram may be created by the CPU 301a of the data processing unit 3.

In the present embodiment, the classifying and counting process of the particles, the determining process of the existence of the nucleated red blood cells, the selecting process of the cluster to be corrected, and the correcting process of the particle number of the selected cluster to be corrected are executed in the data processing unit 3, but the present invention is not limited thereto, and such processes may be executed in the measuring unit 2, the obtained analysis result may be received by the data processing unit 3 and displayed on the display 302.

In the present embodiment, the scattergram is created using the characteristic parameters of the blood cells obtained from the detection signal output from the white blood cell detecting part, and the classifying and counting process of the nucleated red blood cells and the classifying and counting process of the white blood cells are executed based on the created scattergram, but the present invention is not limited thereto, and the classifying and counting process of the nucleated red blood cells and the classifying and counting process of the white blood cells may be executed without creating the scattergram.

In the present embodiment, the two-dimensional scattergram using two of the forward scattered light intensity, the lateral scattered light intensity, and the lateral fluorescence intensity is created, but the present invention is not limited thereto, and a three-dimensional scattergram may be created using the forward scattered light intensity, the lateral scattered light intensity, and the lateral fluorescence intensity.

In the present embodiment, if the nucleated red blood cells are contained in the red blood cell ghost cluster, a correction of subtracting the number of nucleated red blood cells from the particle number of the red blood cell ghost cluster is not performed, but in this case, a correction of subtracting the number of nucleated red blood cells from the particle number of the red blood cell ghost cluster may be performed.

In the present embodiment, when the blood sample containing the nucleated red blood cells is measured, the cluster containing the nucleated red blood cells is selected from the lymphocytes or the neutrophilic leucocytes cluster on the scattergram, and a correction of subtracting the number of nucleated red blood cells from the particle number of the selected cluster is performed, but the present invention is not limited thereto, and when the blood sample containing the immature leucocytes that influence the classifying and counting result of the white blood cells is measured, the cluster containing the immature leucocytes may be selected from the plurality of clusters of the white blood cells on the scattergram, and a correction of subtracting the number of immature leucocytes from the particle number of the selected cluster may be performed. Thus, the present invention is applicable to the sample measurement where it is desired to select the particles to be corrected from the plurality of particles contained in the sample and correct the particle number of the particles using the particle number of other kind of particles.

In the present embodiment, the intensity of fluorescence emitted from the blood cells is used as one of the characteristic parameters of the blood cells, but the present invention is not limited thereto, and the intensity of the absorbed light may be used as the characteristic parameter of the blood cells instead of the fluorescence intensity.

In the present embodiment, an optical measurement of irradiating the light on the measurement sample and obtaining the characteristic parameter of the blood cells is performed, but the present invention is not limited thereto, and DC current may be flowed to the microscopic hole through which the sample is flowed, and the characteristic parameter of the blood cell may be obtained based on the signal indicating change in electrical resistance that occurs when the blood cells pass through the microscopic hole. Moreover, high frequency current may be flowed through the microscopic hole, and the characteristic parameters of the blood cell may be obtained based on the signal indicating change in dielectric constant of the blood cells that occurs when the blood cells pass through the microscopic hole.

In the present embodiment, the CPU 301a of the data processing unit 3 classifies the white blood cells contained in the blood sample into five classifications based on the result of classifying the white blood cells into four classifications and counting the same by the second classifying and counting process, and the result of classifying the white blood cells into two classifications and counting the same by the third classifying and counting process, but the present invention is not limited thereto, and the CPU 301a may classify the white blood cells contained in the blood sample into five classifications based only on the result obtained by the second classifying and counting process.

What is claimed is:
1. A particle analyzer for analyzing a particle in a sample, comprising:
a detecting section configured to detect each of particles contained in a first measurement sample prepared from a sample and a first reagent, and detect each of particles contained in a second measurement sample prepared from the sample and a second reagent different from the first reagent; and
a controller configured to perform operations comprising:
acquiring at least a first and a second characteristic information of each of the particles contained in the first measurement sample based on a first detection result obtained from the first measurement sample, and acquiring at least a third and a fourth characteristic information of each of the particles contained in the second measurement sample based on a second detection result obtained from the second measurement sample;
obtaining a particle number of a specific kind of particles contained in the sample based on at least the acquired first and second characteristic information, and obtaining each particle number of a plural kinds of particles contained in the sample based on at least the acquired third and fourth characteristic information, the plural kinds of particles being different from the specific kind of particles,
determining a target kind of particles, whose particle number is corrected, from the plural kinds of particles, based on at least the acquired third and fourth characteristic information; and
correcting the obtained particle number of the target kind of particles by using the obtained particle number of the specific kind of particles.

2. The analyzer of claim 1, wherein
the controller is configured to perform operations comprising:
generating a particle distribution map for classifying the particles contained in the sample into each particle group of the plural kinds of particles by using at least the third and fourth characteristic information; and
determining the target kind of particles based on particles appearing in a predetermined region in the generated particle distribution map.

3. The analyzer of claim 2, wherein
the predetermined region is a region where the specific kind of particles appear in the particle distribution map.

4. The analyzer of claim 2, wherein
the controller determines the target kind of particles based on the each particle number of the plural kinds of particles appearing in the predetermined region.

5. The analyzer of claim 4, wherein
the controller compares the each particle number of the plural kinds of particles appearing in the predetermined region respectively, and determines a kind of particles with the greatest particle number as the target kind of particles.

6. The analyzer of claim 1, wherein
the controller corrects the particle number of the target kind of particles by subtracting the particle number of the specific kind of particles from the particle number of the target kind of particles.

7. The analyzer of claim 1, wherein
the specific kind of particles are nucleated red blood cells, and the plural kinds of particles comprises lymphocytes and neutrophilic leucocytes.

8. The analyzer of claim 1, wherein
the detection section obtains the first detection result by irradiating light on the first measurement sample, and obtains the second detection result by irradiating light on the second measurement sample.

9. The analyzer of claim 8, wherein
at least one of the first, second, third and fourth characteristic information is an information based on a forward scattered light intensity, a lateral scattered light intensity and a lateral fluorescence intensity.

10. The analyzer of claim 1, wherein
the controller determines whether the particle number of the specific kind of particles is greater than a predetermined number or not,
and corrects the particle number of the target kind of particles when determined that the particle number of the specific kind of particles is greater than the predetermined number.

11. The analyzer of claim 10, further comprising
a display, wherein
the controller displays the corrected particle number and an information indicating that the corrected particle number is obtained by the correction, when the particle number of the target kind of particles has been corrected.

12. A particle analyzer for analyzing a particle in a sample, comprising:
a detecting section configured to detect each of particles contained in a measurement sample prepared from a sample; and
a controller configured to perform operations comprising:
acquiring a plurality of characteristic information of each of the particles contained in the measurement sample based on a detection result by the detection section;
obtaining a particle number of a specific kind of particles contained in the sample and each particle number of a plural kinds of particles contained in the measurement sample, based on the acquired characteristic information, the plural kinds of particles being different from the specific kind of particles;
determining a correction degree for correcting the obtained each particle number of the plural kinds of particles based on the acquired characteristic information; and
correcting the obtained each particle number of the plural kinds of particles, based on the obtained particle number of the specific kind of particles and the determined correction degree.

13. The analyzer of claim 12,
wherein the controller determines a value reflecting a particle number to be subtracted from the each particle number of the plural kinds of particles as the correction degree, and corrects the each particle number of the plural kinds of particles by subtracting, according to the value, the particle number of the specific kind of the particles from the each particle number of the plural kinds of particles.

14. The analyzer of claim 12, wherein
the controller generates a particle distribution map for classifying particles contained in the sample into each particle group of the plural kinds of particles by using at least two characteristic information of the plurality of characteristic information,
and determines the correction degree based on particles appearing in a predetermined region of the particle distribution map.

15. The analyzer of claim 14,
wherein the controller is configured to perform operations comprising:
determining a ratio of the each particle number of the plural kinds of particles appearing in the predetermined region as the correction degree;
dividing the particle number of the specific kind of particles with respect to every plural kinds of particles according to the determined ratio; and
subtracts the divided particle number from corresponding each particle number of the plural kinds of particles.

16. A particle analyzing method for analyzing a particle in a sample, comprising steps of:
(a) detecting each of particles contained in a first measurement sample prepared from a sample and a first reagent, and detecting each of particles contained in a second measurement sample prepared from the sample and a second reagent different from the first reagent;
(b) acquiring at least a first and a second characteristic information of each of the particles contained in the first measurement sample based on a first detection result obtained from the first measurement sample, and acquiring at least a third and a fourth characteristic information of each of the particles contained in the second measurement sample based on a second detection result obtained from the second measurement sample;
(c) obtaining a particle number of a specific kind of particles contained in the sample based on at least the acquired first and second characteristic information, and obtaining each particle number of a plural kinds of particles contained in the sample based on at least the acquired third and fourth characteristic information, the plural kinds of particles being different from the specific kind of particles;
(d) determining a target kind of particles, whose particle number is corrected, from the plural kinds of particles, based on at least the acquired third and fourth information; and
(e) correcting the obtained particle number of the target kind of particles by using the obtained particle number of the specific kind of particles.

17. A particle analyzer for analyzing a particle in a sample, comprising:
a flow cell through which each of a first measurement sample and a second measurement sample passes, wherein the first measurement sample is prepared by a sample and a first reagent, and the second measurement sample is prepared by the sample and a second reagent different from the first reagent;
a first scattered light detector that detects a first scattered light from each of particles contained in a measurement sample passing through the flow cell;
a second scattered light detector that detects a second scattered light from each of particles contained in a measurement sample passing through the flow cell, wherein a direction of the second scattered light is different from that of the first scattered light;
a fluorescence detector that detects a fluorescence from each of particles contained in a measurement sample passing through the flow cell; and
a controller configured to perform operations comprising:
acquiring a first characteristic information of each of particles contained in the first measurement sample based on a fluorescence detected from the first measurement sample, and acquiring a second characteristic information of each of the particles contained in the first measurement sample based on one of a first and a second scattered light detected from the first measurement sample;

acquiring a third characteristic information of each of particles contained in the second measurement sample based on a fluorescence detected from the second measurement sample, and acquiring a fourth characteristic information of each of the particles contained in the second measurement sample based on one of a first and a second scattered light detected from the second measurement sample;

obtaining a particle number of a specific kind of particles contained in the sample based on at least the acquired first and second characteristic information, and obtaining each particle number of a plural kinds of particles contained in the sample based on at least the acquired third and fourth characteristic information, the plural kinds of particles being different from the specific kind of particles;

determining a target kind of particles, whose particle number is corrected, from the plural kinds of particles, based on at least the acquired third and fourth characteristic information; and correcting the obtained particle number of the target kind of particles by using the obtained particle number of the specific kind of particles.

18. The analyzer of claim 17, wherein the specific kind of particles are nucleated red blood cells, and the plural kinds of particles comprises lymphocytes and neutrophilic leucocytes.

19. The analyzer of claim 17, wherein the first scattered light is a forward scattered light, and the second scattered light is a lateral scattered light.

20. The analyzer of claim 19, wherein each of the first and the third characteristic information is a fluorescence intensity;
the second characteristic information is a forward scattered light intensity; and
the fourth characteristic information is a lateral scattered light intensity.

* * * * *